(12) United States Patent
Kobayashi et al.

(10) Patent No.: US 11,883,563 B2
(45) Date of Patent: Jan. 30, 2024

(54) RESIN COMPOSITION, FLEXIBLE TUBE, ACOUSTIC LENS, AND SHEATH FOR MEDICAL DEVICE TO BE SUBJECTED TO GAS LOW-TEMPERATURE STERILIZATION AND MEDICAL DEVICE TO BE SUBJECTED TO GAS LOW-TEMPERATURE STERILIZATION

(71) Applicant: OLYMPUS CORPORATION, Hachioji (JP)

(72) Inventors: Koji Kobayashi, Tokyo (JP); Takayuki Kondo, Tokyo (JP); Rieko Niino, Tokyo (JP); Masaya Iwamoto, Yamato (JP)

(73) Assignee: OLYMPUS CORPORATION, Tokyo (JP)

( * ) Notice: Subject to any disclaimer, the term of this patent is extended or adjusted under 35 U.S.C. 154(b) by 792 days.

(21) Appl. No.: 16/856,468

(22) Filed: Apr. 23, 2020

(65) Prior Publication Data
US 2020/0246510 A1 Aug. 6, 2020

Related U.S. Application Data

(63) Continuation of application No. PCT/JP2018/033030, filed on Sep. 6, 2018.

(30) Foreign Application Priority Data

Oct. 26, 2017 (JP) .................................. 2017-207422

(51) Int. Cl.
*A61L 29/06* (2006.01)
*A61B 1/00* (2006.01)
(Continued)

(52) U.S. Cl.
CPC .......... *A61L 29/06* (2013.01); *A61B 1/00096* (2013.01); *A61L 2/14* (2013.01);
(Continued)

(58) Field of Classification Search
USPC ........................................................... 521/28
See application file for complete search history.

(56) References Cited

U.S. PATENT DOCUMENTS 3,876,565 A * 4/1975 Takashima ............. B01J 47/018
521/29
4,612,340 A 9/1986 Ohachi
(Continued)

FOREIGN PATENT DOCUMENTS

CN 106165448 A 11/2016
JP 59164066 A 9/1984
(Continued)

OTHER PUBLICATIONS

Chinese Office Action (and English translation thereof) dated Aug. 10, 2021, issued in counterpart Chinese Application No. 201880067547.X.
(Continued)

*Primary Examiner* — Fred M Teskin
(74) *Attorney, Agent, or Firm* — Holtz, Holtz & Volek PC

(57) ABSTRACT

A resin composition for a medical device to be subjected to gas low-temperature sterilization includes a resin and an ion exchanger.

19 Claims, 6 Drawing Sheets

(51) Int. Cl.
  *A61L 2/14*  (2006.01)
  *A61L 2/20*  (2006.01)
  *A61L 29/04*  (2006.01)
  *C08F 236/06*  (2006.01)
  *C08L 25/06*  (2006.01)
  *C08L 27/12*  (2006.01)
  *C08L 63/00*  (2006.01)
  *C08L 67/00*  (2006.01)
  *C08L 83/04*  (2006.01)

(52) U.S. Cl.
  CPC ............ *A61L 2/208* (2013.01); *A61L 29/041* (2013.01); *C08F 236/06* (2013.01); *C08L 25/06* (2013.01); *C08L 27/12* (2013.01); *C08L 63/00* (2013.01); *C08L 67/00* (2013.01); *C08L 83/04* (2013.01); *A61L 2202/24* (2013.01)

(56) References Cited

U.S. PATENT DOCUMENTS

| | | | |
|---|---|---|---|
| 10,308,582 B2 * | 6/2019 | Binder | ............... B01J 43/00 |
| 10,370,532 B2 | 8/2019 | Kobayashi et al. | |
| 2007/0166642 A1 * | 7/2007 | Inoue | ............... G03F 7/0388 |
| | | | 430/270.1 |
| 2014/0128669 A1 * | 5/2014 | Kobayashi | ............... C08L 33/04 |
| | | | 600/101 |

FOREIGN PATENT DOCUMENTS

| | | | |
|---|---|---|---|
| JP | 2001293082 A | 10/2001 | |
| JP | 2003004638 A | 1/2003 | |
| JP | 2004018459 A | 1/2004 | |
| JP | 2005247895 A | 9/2005 | |
| JP | 5374154 B2 | 9/2013 | |
| JP | 2015155515 A | 8/2015 | |
| JP | 2018517045 A | 6/2018 | |
| WO | 2016198372 A1 | 12/2016 | |
| WO | 2018155285 A1 | 8/2018 | |

OTHER PUBLICATIONS

International Search Report (ISR) (and English translation thereof) dated Nov. 13, 2018 issued in International Application No. PCT/JP2018/033030.

* cited by examiner

RESIN COMPOSITION, FLEXIBLE TUBE, ACOUSTIC LENS, AND SHEATH FOR MEDICAL DEVICE TO BE SUBJECTED TO GAS LOW-TEMPERATURE STERILIZATION AND MEDICAL DEVICE TO BE SUBJECTED TO GAS LOW-TEMPERATURE STERILIZATION

This application is a continuation application of PCT International Application No. PCT/JP2018/033030, filed on Sep. 6, 2018, whose priority is claimed on Japanese Patent Application No. 2017-207422, filed in Japan on Oct. 26, 2017. The contents of both the PCT International Application and the Japanese Application are incorporated herein by reference.

BACKGROUND

Field of the Invention

The present invention relates to a resin composition, a flexible tube, an acoustic lens, and a sheath for a medical device to be subjected to gas low-temperature sterilization and a medical device to be subjected to gas low-temperature sterilization.

Description of Related Art

A medical device is subjected to sterilization treatment. For this reason, parts or members included in a medical device require resistance (sterilization resistance) to a sterilization action that is applied to components in the sterilization treatment.

For example, Japanese Patent No. 5374154 discloses a medical resin composition, a resin pellet, and a medical part that have excellent color-change stability with respect to a radiation sterilization method using a y ray or an electron beam. Japanese Patent No. 5374154 discloses that a silane compound is included in a thermoplastic resin as a radiation resistant agent to improve sterilization resistance.

For example, Japanese Unexamined Patent Application, First Publication No. 2005-247895 discloses a medical resin composition that includes a hydrogenated diene-based copolymer and a polyolefin resin having a peak melting temperature in the range of 100 to 200° C. in order to improve sterilization resistance to high-pressure steam sterilization.

In recent years, gas low-temperature sterilization has been widely used as sterilization treatment for a medical device. For example, sterilization gas, such as hydrogen peroxide gas, is often used in the gas low-temperature sterilization.

The techniques disclosed in Japanese Patent No. 5374154 and Japanese Unexamined Patent Application, First Publication No. 2005-247895 relate to resin compositions that have good sterilization resistance to radiation sterilization and high-pressure steam sterilization, respectively. Accordingly, the techniques disclosed in Japanese Patent No. 5374154 and Japanese Unexamined Patent Application, First Publication No. 2005-247895 are not techniques that can improve sterilization resistance to, particularly, gas low-temperature sterilization.

There is a strong demand for a resin composition for a medical device that has good sterilization resistance to gas low-temperature sterilization.

SUMMARY

According to a first aspect of the present invention, a resin composition for a medical device to be subjected to gas low-temperature sterilization of a first aspect of the invention includes: at least one resin selected from a group consisting of silicone, acrylic, polyethylene, polyetheretherketone, polytetrafluoroethylene, tetrafluoroethylene, polyvinylidene fluoride, polychlorotrifluoroethylene, chlorotrifluoroethylene, polyamide, polycarbonate, polystyrene, urethane, polyurethane, polyphenylsulfone, polyethersulfone, polysulfone, polypropylene, polyacetal, polybenzimidazole, polyvinyl chloride, polyester, fluorinated elastomer, polybutadiene, and polyepoxy elastomer; and an ion exchanger.

According to a second aspect of the present invention, in the resin composition for a medical device to be subjected to gas low-temperature sterilization according to the first aspect, the ion exchanger may contain an inorganic substance that discharges at least one of a hydroxide ion and a proton.

According to a third aspect of the present invention, in the resin composition for a medical device to be subjected to gas low-temperature sterilization according to the first aspect, a content of the ion exchanger may be in a range of 0.01 parts by mass to 40 parts by mass with respect to 100 parts by mass of the resin.

According to a fourth aspect of the present invention, a medical device to be subjected to gas low-temperature sterilization includes the resin composition according to the first aspect.

According to a fifth aspect of the present invention, a flexible tube for a medical device to be subjected to gas low-temperature sterilization includes the resin composition according to the first aspect, and the resin includes at least one resin selected from a group consisting of polyester, polystyrene, polybutadiene, and polyepoxy.

According to a sixth aspect of the present invention, a medical device to be subjected to gas low-temperature sterilization includes the flexible tube according to the fifth aspect.

According to a seventh aspect of the present invention, a flexible tube for a medical device to be subjected to gas low-temperature sterilization includes the resin composition according to the first aspect, and the resin includes fluorinated elastomer.

According to an eighth aspect of the present invention, a medical device to be subjected to gas low-temperature sterilization includes the flexible tube according to the seventh aspect.

According to a ninth aspect of the present invention, an acoustic lens for a medical device to be subjected to gas low-temperature sterilization includes the resin composition according to the first aspect, and the resin includes silicone.

According to a tenth aspect of the present invention, a medical device to be subjected to gas low-temperature sterilization includes the acoustic lens according to the ninth aspect.

According to an eleventh aspect of the present invention, a sheath for a medical device to be subjected to gas low-temperature sterilization includes the resin composition according to the first aspect, and the resin includes fluorinated elastomer.

According to a twelfth aspect of the present invention, a medical device to be subjected to gas low-temperature sterilization includes the sheath according to the eleventh aspect.

DETAILED DESCRIPTION OF EMBODIMENTS

Figure 1:
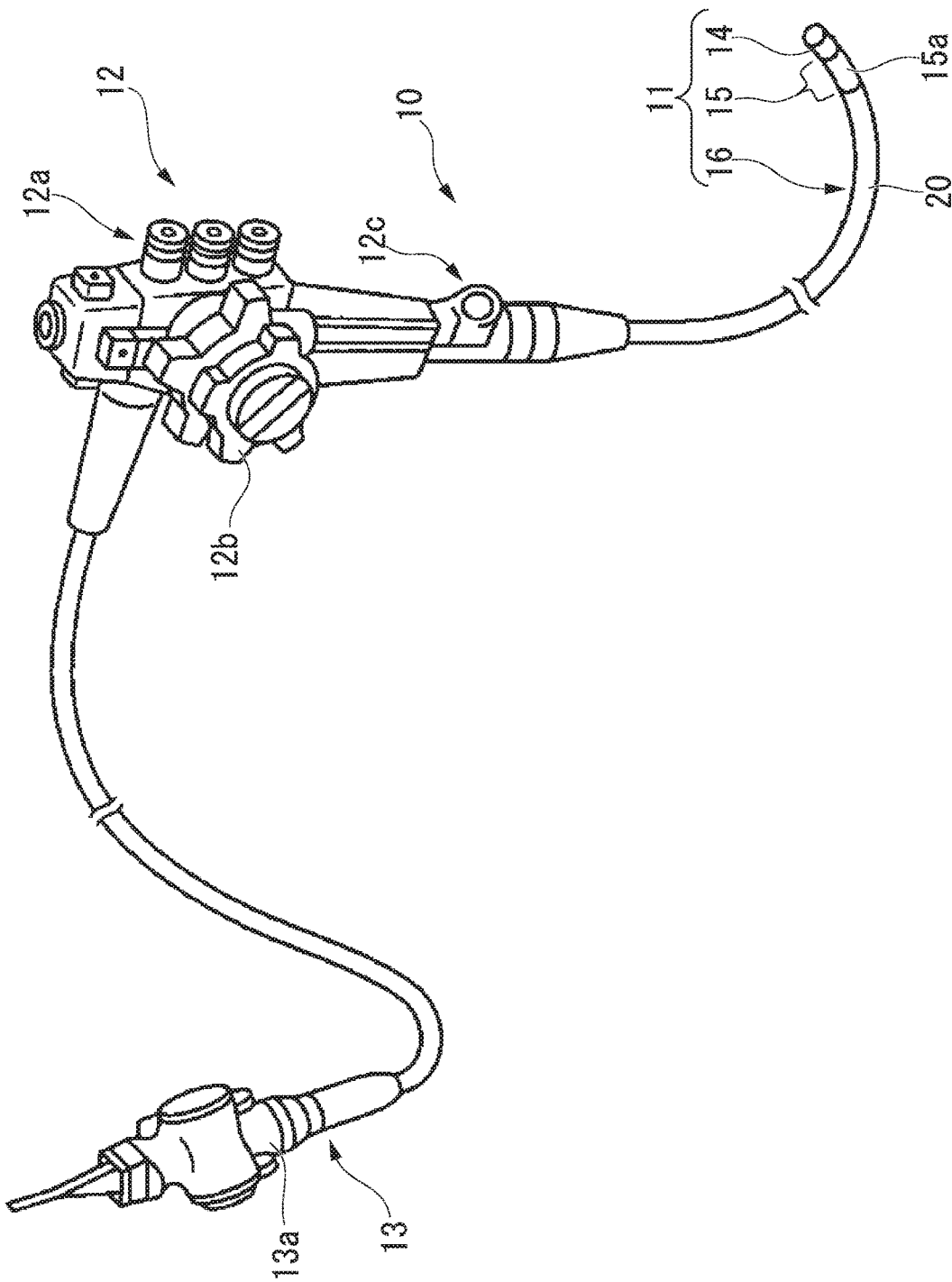
FIG. 1 is a schematic perspective view showing an example of the configuration of an endoscope that is a medical device of a first embodiment of the invention.

Embodiments of the invention will be described below with reference to the accompanying drawings. The same or corresponding members will be denoted in all drawings by the same reference numerals even in different embodiments, and description common thereto will be omitted.

First Embodiment

A resin composition for a medical device to be subjected to gas low-temperature sterilization and a medical device to be subjected to gas low-temperature sterilization of a first embodiment of the invention will be described below.

Figure 2:
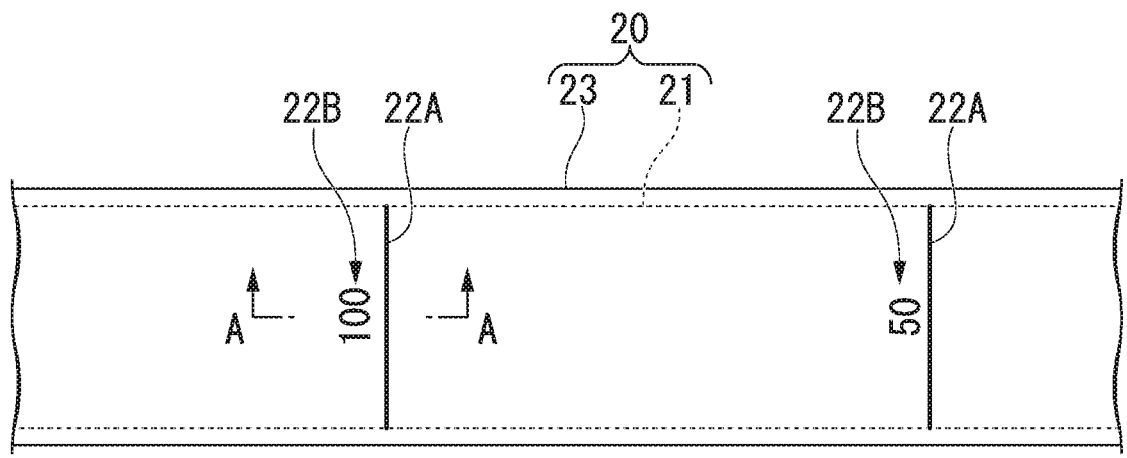
FIG. 2 is a schematic plan view showing an example of the structure of a flexible tube of an insertion unit of the endoscope that is the medical device of the first embodiment of the invention.
Figure 3:
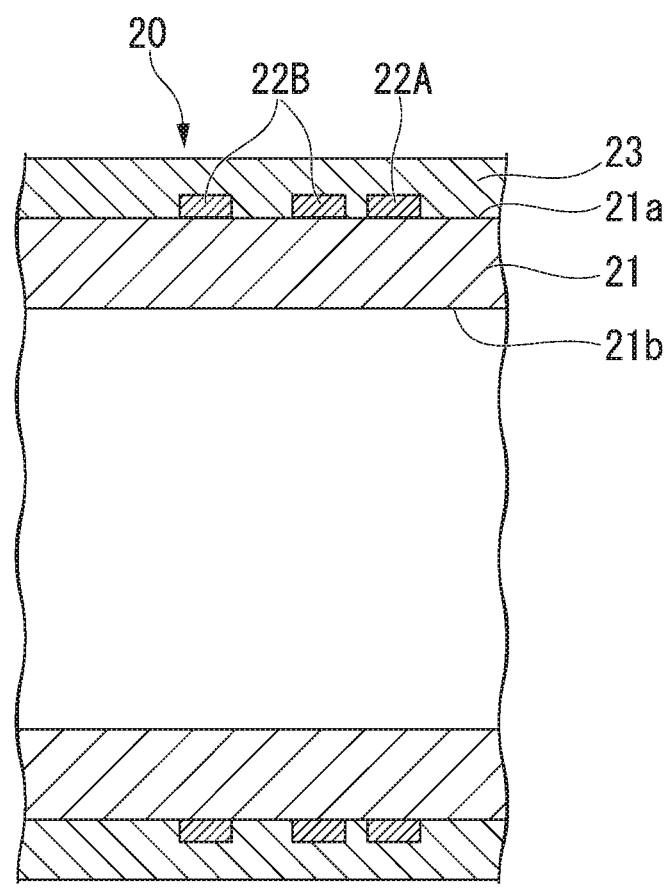
FIG. 3 is a cross-sectional view taken along line A-A of FIG. 2.
Figure 4:
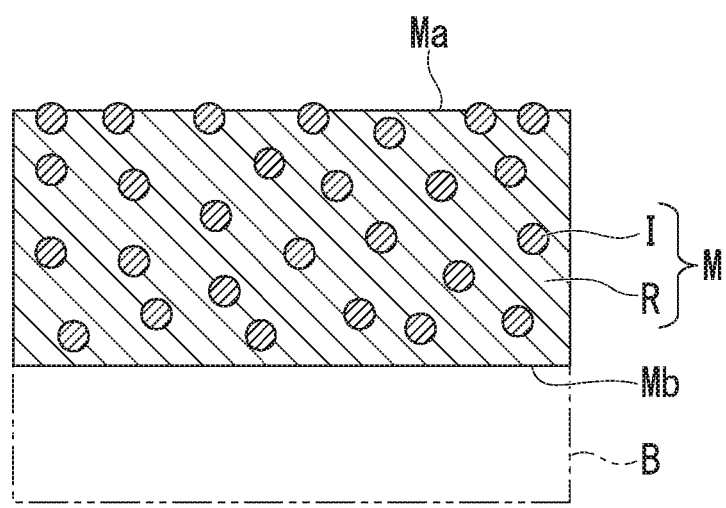
FIG. 4 is a schematic cross-sectional view showing an example of the structure of a resin composition of the first embodiment of the invention.

FIG. 1 is a schematic perspective view showing an example of the configuration of an endoscope that is a medical device of a first embodiment of the invention. FIG. 2 is a schematic plan view showing an example of the structure of a flexible tube of an insertion unit of the endoscope that is the medical device of the first embodiment of the invention. FIG. 3 is a cross-sectional view taken along line A-A of FIG. 2. FIG. 4 is a schematic cross-sectional view showing an example of the structure of a resin composition of the first embodiment of the invention.

An endoscope 10 (medical device) of this embodiment shown in FIG. 1 is a medical endoscope that is used while being inserted into the body of a patient. The endoscope 10 is a medical device to be subjected to gas low-temperature sterilization. The type of gas low-temperature sterilization is not particularly limited. Examples of gas low-temperature sterilization suitable for the endoscope 10 include hydrogen peroxide low-temperature plasma sterilization, hydrogen peroxide gas low-temperature sterilization, and the like. Specific examples of a sterilization device used for the gas low-temperature sterilization include STERRAD (registered trademark) NX (registered trademark) (trade name; manufactured by Johnson & Johnson K.K.), V-PRO (registered trademark) maX (trade name; manufactured by STERIS Japan Inc.), STERIZONE (registered trademark) (trade name; manufactured by T503 inc.), and the like.

The endoscope 10 includes an insertion unit 11 and an operation unit 12.

The insertion unit 11 is formed in the form of a flexible tube in order to be inserted into the body of a patient. The insertion unit 11 includes a distal end part 14, a bendable part 15, and a flexible tube part 16 that are arranged in this order from the distal end side in an insertion direction. Although not shown in FIG. 1, for example, long built-in elements, such as a treatment tool channel, a light guide, an image transmission cable, and operation wires, are inserted into the insertion unit 11.

The distal end part 14 is disposed at a portion that includes the most distal end of the endoscope 10. The distal end part 14 includes an end effector of the endoscope 10 that functions as a manipulator. For example, in this embodiment, an image pickup element, such as a CCD, and an image pickup optical system including an appropriate lens are provided in the distal end part 14 in order to acquire the video of an object to be examined. In this embodiment, the distal end part 14 has a columnar appearance.

The image pickup element is disposed on the image surface of the image pickup optical system. The image pickup element photoelectrically converts received light to generate image signals.

The image signals generated by the image pickup element are transmitted to the operation unit 12 to be described later through metal wires. The image signals may be subjected to signal processing as necessary before being transmitted to the operation unit 12.

The metal wires include a signal line and a power line. The signal line supplies a control signal to the image pickup element. The power line supplies a drive voltage to the image pickup element. The metal wires are put together in a cable.

However, the image pickup element may be disposed in the operation unit 12 to be described later. In this case, the distal end of an image guide fiber, which transmits a light image to the image pickup element, is disposed on the image surface of the image pickup optical system. The image guide fiber extends up to the operation unit 12, in which the image pickup element is disposed, via the inside of the bendable part 15 and the flexible tube part 16 to be described later. An optical fiber may be used as the image guide fiber.

In this way, an image acquired by the distal end part 14 is transmitted as image signals or image light through the image transmission cable, which is formed of the metal wires or the optical fiber, in the endoscope 10.

Although not shown, an image pickup window, an illumination window, an opening, and the like are provided at the distal end of the distal end part 14. The opening communicates with the treatment tool channel.

The bendable part 15 is connected to the proximal end of the distal end part 14. The bendable part 15 is a tubular portion that is adapted to be bendable in order to change the direction of the distal end part 14.

The bendable part 15 includes, for example, a plurality of annular nodal rings. The plurality of nodal rings are rotatably connected to each other. Operation wires are inserted into the plurality of nodal rings.

For example, members, such as electrical wires connected to the image pickup element of the distal end part 14 and a light guide fiber extending up to the illumination window, are housed in the bendable part 15.

The members (hereinafter, referred to as long members), such as the operation wires, the image transmission cable, and the light guide fiber having been described above, are inserted into the flexible tube part 16 to be described later and extend up to the operation unit 12 to be described later.

The bendable part 15 is covered with a sheath tube 15a (a flexible tube, a sheath) made of a resin.

The sheath tube 15a is made of a resin material, which is excellent in flexibility, in order to make the bending operation of the bendable part 15 be smooth. In addition, it is more preferable that the sheath tube 15a is made of a resin material having a low coefficient of friction allowing the bendable part 15 to be smoothly inserted into the body of a patient. It is more preferable that the coefficient of friction of the sheath tube 15a has a value allowing the sheath tube 15a to have low friction on other medical devices likely to be in contact with the sheath tube 15a and on the body cavity of a patient.

The flexible tube part 16 is a tubular part that connects the bendable part 15 to the operation unit 12 to be described later.

The flexible tube part 16 includes a flexible tube 20 that forms an outer peripheral portion. The above-mentioned long members are inserted into the inner cavity of the flexible tube 20.

As shown in FIGS. 2 and 3, the flexible tube 20 includes at least a tube body 21 (flexible tube) and a coating layer 23 (sheath).

An example of the cross-section of the tube body 21 and the coating layer 23 is shown in FIG. 3. However, members positioned on the inner side than an inner peripheral surface 21b of the tube body 21 are not shown in FIG. 3.

The tube body 21 is formed of a tube member that is made of a flexible resin.

A reinforcing member may be provided inside the inner peripheral surface 21b of the tube body 21 in order to keep the circular cross-section of the inner cavity of the flexible tube 20 in a case where the flexible tube 20 is bent. Examples of such a reinforcing member include a flex that is a spirally wound belt-like member, a net-like metal blade, and the like. Metal or a resin is used as the material of the belt-like member of the flex.

Indexes 22A and 22B are formed on an outer peripheral surface 21a (see FIG. 3) of the tube body 21 of the flexible tube 20. The indexes 22A and 22B are marks that can be visually recognized from the outside of the flexible tube 20. The indexes 22A and 22B are provided in order to allow an operator to visually check the insertion length of the flexible tube 20 in, for example, a case where the flexible tube 20 is inserted into the body of a patient. In the example shown in FIG. 2, the index 22A is a line extending in the circumferential direction of the tube body 21. In the example shown in FIG. 2, the indexes 22B are numerals representing a length up to the distal end part 14 (see FIG. 1) from the index 22A.

A plurality of indexes 22A and 22B are formed at an appropriate pitch of, for example, 50 mm in the longitudinal direction of the tube body 21.

The indexes 22A and 22B formed using paint that is colored with a color material. The color of the indexes 22A and 22B is different from the color of the outer peripheral surface 21a of the tube body 21.

The coating layer 23 is provided in the form of a layer, which covers all the tube body 21 and the indexes 22A and 22B, in order to protect the tube body 21 and the indexes 22A and 22B. The coating layer 23 is a sheath that forms the outermost surface of the flexible tube 20.

The coating layer 23 is made of a material having good optical transparency in order to allow the indexes 22A and 22A to be easily visually recognized. For example, it is more preferable that the coating layer 23 has a light transmittance of 50% or more at the wavelength of visible light.

It is more preferable that the coating layer 23 is made of a resin material having excellent flexibility in order to make the flexibility of the flexible tube 20 be good. In addition, it is more preferable that the resin material used for the coating layer 23 has a low coefficient of friction allowing the flexible tube 20 to be smoothly inserted into the body of a patient.

It is more preferable that the coefficient of friction of the coating layer 23 has a value allowing the coating layer 23 to have low friction on other medical devices likely to be in contact with the coating layer 23 and on the body cavity of a patient.

As shown in FIG. 1, the operation unit 12 is part of the device that is used by an operator in order to operate the endoscope 10. Examples of an operation using the operation unit 12 can include an operation for pulling operation wires (not shown) in order to change the amount of bending of the bendable part 15. The operation unit 12 includes, for example, an operation switch 12a, operation knobs 12b, and the like.

A forceps valve 12c is provided on the distal end side of the operation unit 12 in order to allow a treatment tool, a catheter, and the like to be inserted into the treatment tool channel.

A universal cord 13, which connects a power line, a signal line, and the like required for the operation of the endoscope 10 to an external device, is connected to the proximal end portion of the operation unit 12.

A connector part 13a, which is to be connected to an external device, is provided at the proximal end portion of the universal cord 13.

In the endoscope 10 having been described above, the resin composition of this embodiment is used for some or all of structural members made of a resin in order to improve sterilization resistance to gas low-temperature sterilization.

As schematically shown in FIG. 4, a resin composition M of this embodiment includes a matrix resin R (resin) and an ion exchanger I. The resin composition M may further contain additives, such as a friction reducing agent, a filler, a cross-linker, a plasticizer, a reinforcing agent, and a coloring agent.

The matrix resin R includes at least one resin selected from the group consisting of silicone, acrylic, polyethylene, polyetheretherketone, polytetrafluoroethylene, tetrafluoroethylene, polyvinylidene fluoride, polychlorotrifluoroethylene, chlorotrifluoroethylene, polyamide, polycarbonate, polystyrene, urethane, polyurethane, polyphenylsulfone, polyethersulfone, polysulfone, polypropylene, polyacetal, polybenzimidazole, polyvinyl chloride, polyester, fluorinated elastomer, polybutadiene, and polyepoxy elastomer.

The matrix resin R may be a hard resin including the above-mentioned at least one resin, or may be elastomer that includes the above-mentioned at least one resin in the components thereof. The matrix resin R may be a mixture of a hard resin and elastomer.

The ion exchanger I is used in order to improve the sterilization resistance of the matrix resin R.

The inventors have investigated the composition of the matrix resin R in earnest in order to further improve the sterilization resistance of the matrix resin R to the gas low-temperature sterilization treatment using sterilization gas. The inventors have newly found that the sterilization resistance of the matrix resin R can be significantly improved in a case where the resin composition M contains an ion exchanger. As a result, the inventors have reached the invention.

The mechanism of the action of the sterilization gas in the gas low-temperature sterilization is complex. Accordingly, it is not thought that only the presence of ions in the sterilization gas contributes to a chemical reaction related to sterilization in the gas low-temperature sterilization. However, according to the inventors' investigation, better sterilization resistance is obtained in a case where an ion exchanger is contained in the resin composition M.

The type of the ion exchanger I may be any one of a cation exchanger, an anion exchanger, and an amphoteric ion exchanger. However, it is more preferable that the ion exchanger I is an amphoteric ion exchanger.

Examples of a particularly preferred ion exchanger I include a composition containing an inorganic substance that can discharge at least one of a hydroxide ion and a proton.

For example, inorganic compounds including at least one type of metal atoms among bismuth (Bi), antimony (Sb), zirconium (Zr), magnesium (Mg), and aluminum (Al) may be used as the ion exchanger I.

For example, specific examples of a cation exchanger suitable as the ion exchanger I include IXE (registered trademark)-300 (trade name; manufactured by Toagosei Co., Ltd., Sb-based compound), IXE (registered trademark)-100 (trade name; manufactured by Toagosei Co., Ltd., Zr-based compound), and the like.

For example, specific examples of an anion exchanger suitable as the ion exchanger I include IXE (registered trademark)-770D (trade name; manufactured by Toagosei Co., Ltd., Mg—Al-based compound), IXE (registered trademark)-800 (trade name; manufactured by Toagosei Co., Ltd., Zr-based compound), and the like.

For example, specific examples of the amphoteric ion exchanger suitable as the ion exchanger I include IXE (registered trademark)-600 (trade name; manufactured by Toagosei Co., Ltd., Sb—Bi-based compound), IXE (registered trademark)-633 (trade name; manufactured by Toagosei Co., Ltd., Sb—Bi-based compound), IXE (registered trademark)-6107 (trade name; manufactured by Toagosei Co., Ltd., Zr—Bi-based compound), IXE (registered trademark)-6136 (trade name; manufactured by Toagosei Co., Ltd., Zr—Bi-based compound), IXEPLAS (registered trademark)-A1 (trade name; manufactured by Toagosei Co., Ltd., Zr—Mg—Al-based compound), IXEPLAS (registered trademark)-A2 (trade name; manufactured by Toagosei Co., Ltd., Zr—Mg—Al-based compound), IXEPLAS (registered trademark)-B1 (trade name; manufactured by Toagosei Co., Ltd., Zr—Bi-based compound), and the like.

It is more preferable that the content of the ion exchanger I in the resin composition M is in the range of 0.01 parts by mass to 40 parts by mass with respect to 100 parts by mass of the matrix resin R.

There is a concern that it may be difficult for a chemical reaction between the sterilization gas and the matrix resin R to be suppressed in a case where the content of the ion exchanger I is less than 0.01 parts by mass.

Since the content of the ion exchanger I is excessively high with respect to the matrix resin R in a case where the content of the ion exchanger I exceeds 40 parts by mass, there is a concern that the mechanical characteristics, appearance, and the like of the resin composition M may deteriorate excessively. For example, in a case where the content of the ion exchanger I as inorganic particles is excessively high, the flexibility of the resin composition M is lowered. As a result, there is a concern that mechanical characteristics, such as tensile strength and flexibility, may deteriorate. In addition, there is a concern that the appearance of the resin composition M may deteriorate in a case where the content of the granular ion exchanger I is excessively high. For example, since transparency is damaged in a case where the content of the granular ion exchanger I is excessively high, there is a concern that the appearance of the resin composition M may deteriorate. For example, since the amount of the exposure of the ion exchanger I to the surface is increased in a case where the content of the granular ion exchanger I is excessively high, there is a concern that the appearance of the resin composition M may deteriorate.

For example, the resin composition M may be manufactured by molding using a molding material. A fluid or solid resin material, which forms the matrix resin R, and the ion exchanger I are mixed in the molding material. Examples of a molding method used for molding include injection molding, extrusion molding, and blow molding that use appropriate molds, and the like. Appropriate curing methods, such as thermal curing and ultraviolet curing, may be used depending on the resin material as a method of curing a molding material.

The resin composition M manufactured by molding may be bonded and fixed to a base material B (see a two-dot chain line of FIG. 4) by, for example, an appropriate adhesive layer (not shown) provided on a surface Mb.

For example, a material to be applied may be applied to the base material B and then cured to manufacture the resin composition M. A liquid resin material, which forms the matrix resin R, and the ion exchanger I are mixed in the material to be applied. Appropriate curing methods, such as thermal curing and ultraviolet curing, may be used depending on the resin material as a method of curing the material to be applied.

For example, the resin composition M may be in contact with the base material B without being fixed to the base material B.

In the resin composition M manufactured as described above, the granular ion exchanger I is dispersed in the matrix resin R. Part of the ion exchanger I is exposed to the outside on, for example, a surface Ma.

The resin composition M of this embodiment may be used for any of the structural members, which are made of a resin, of the endoscope 10.

For example, the resin composition M may form the tube body 21. In this case, elastomer that includes at least one resin selected from the group consisting of polyester, polystyrene, polybutadiene, and polyepoxy, and the like may be used as the matrix resin R.

For example, the resin composition M may form the coating layer 23. In this case, fluorinated elastomer, which is formed in a case where a fluorinated coating agent is cured, and the like may be used as the matrix resin R.

For example, the resin composition M may form the sheath tube 15a. In this case, fluorinated elastomer and the like may be used as the matrix resin R.

For example, the resin composition M may be used for an appropriate resin molding and an appropriate resin tube forming the operation unit 12 and the universal cord 13. In this case, a polysulfone resin, a polyamide resin, and the like may be used as the matrix resin R.

The resin composition M may be used for the above-mentioned long members that are inserted into the flexible tube 20.

Next, the action of the resin composition M will be mainly described with regard to the action of the endoscope 10.

The resin composition M has a structure where the ion exchanger I is dispersed in the matrix resin R. In the resin composition M, part of the ion exchanger I is exposed to the outside on the surface of the matrix resin R.

Since there is a concern that microorganisms and the like as an object to be subjected to sterilization may adhere to the endoscope 10, the endoscope 10 is used after being subjected to gas low-temperature sterilization.

In a case where the gas low-temperature sterilization of the endoscope 10 is started, for example, sterilization gas, ions and radical components derived from sterilization gas, and the like (hereinafter, referred to "sterilization gas and the like") chemically attack the object to be subjected to sterilization. As a result, the object to be subjected to sterilization is destroyed. In a case where the sterilization gas and the like are in contact with the respective structural members of the endoscope 10, there is a possibility that the sterilization gas and the like also chemically react with the respective structural members. Particularly, the resin material is likely to be chemically attacked by the sterilization gas and the like.

A detailed reaction mechanism is not clear. However, according to the inventors' experimental investigation, chemical attack on the matrix resin R is significantly reduced since the ion exchanger I is included in the resin composition M. As a result, the deterioration of the matrix resin R is suppressed.

It is thought that the reason for this is as follows.

For example, it is thought that the ion exchanger I exchanges and traps ions of products derived from sterilization gas during the exchange of ions.

For example, it is thought that ions discharged from the ion exchanger I at the time of exchange of ions react with sterilization gas and the like.

It is thought that chemical attack on the matrix resin R is suppressed since reactive components included in the sterilization gas and the like are reduced in the matrix resin R around the ion exchanger I in this way.

It is thought that both cations and anions are generated during the generation of products contributing to the chemical reaction with the matrix resin R. Accordingly, as long as the ion exchanger I can exchange at least any of cations and anions, chemical attack caused by the sterilization gas and the like can be suppressed. However, in a case where the ion exchanger I is an amphoteric ion exchanger, products contributing to a chemical reaction or chemical attack can be more efficiently reduced. Accordingly, it is more preferable that the ion exchanger I is an amphoteric ion exchanger.

According to the inventors' investigation, particularly, in a case where the sterilization gas is hydrogen peroxide gas and the ion exchanger I contains an inorganic substance that can discharge at least one of a hydroxide ion and a proton, at least one of an acidic atmosphere and a basic atmosphere can be neutralized. As a result, chemical attack is further suppressed.

As described above, the endoscope 10 of this embodiment includes the resin composition M. As a result, the sterilization resistance of the endoscope 10 to gas low-temperature sterilization is improved. Accordingly, the life of the endoscope 10 is improved.

Particularly, in a case where the resin composition M is used for structural members exposed to the outer surface of the endoscope 10, the chemical attack of the sterilization gas and the like on members provided in the endoscope 10 is suppressed by the resin composition M.

Second Embodiment

Next, a medical device to be subjected to gas low-temperature sterilization of a second embodiment of the invention will be described.

Figure 5:
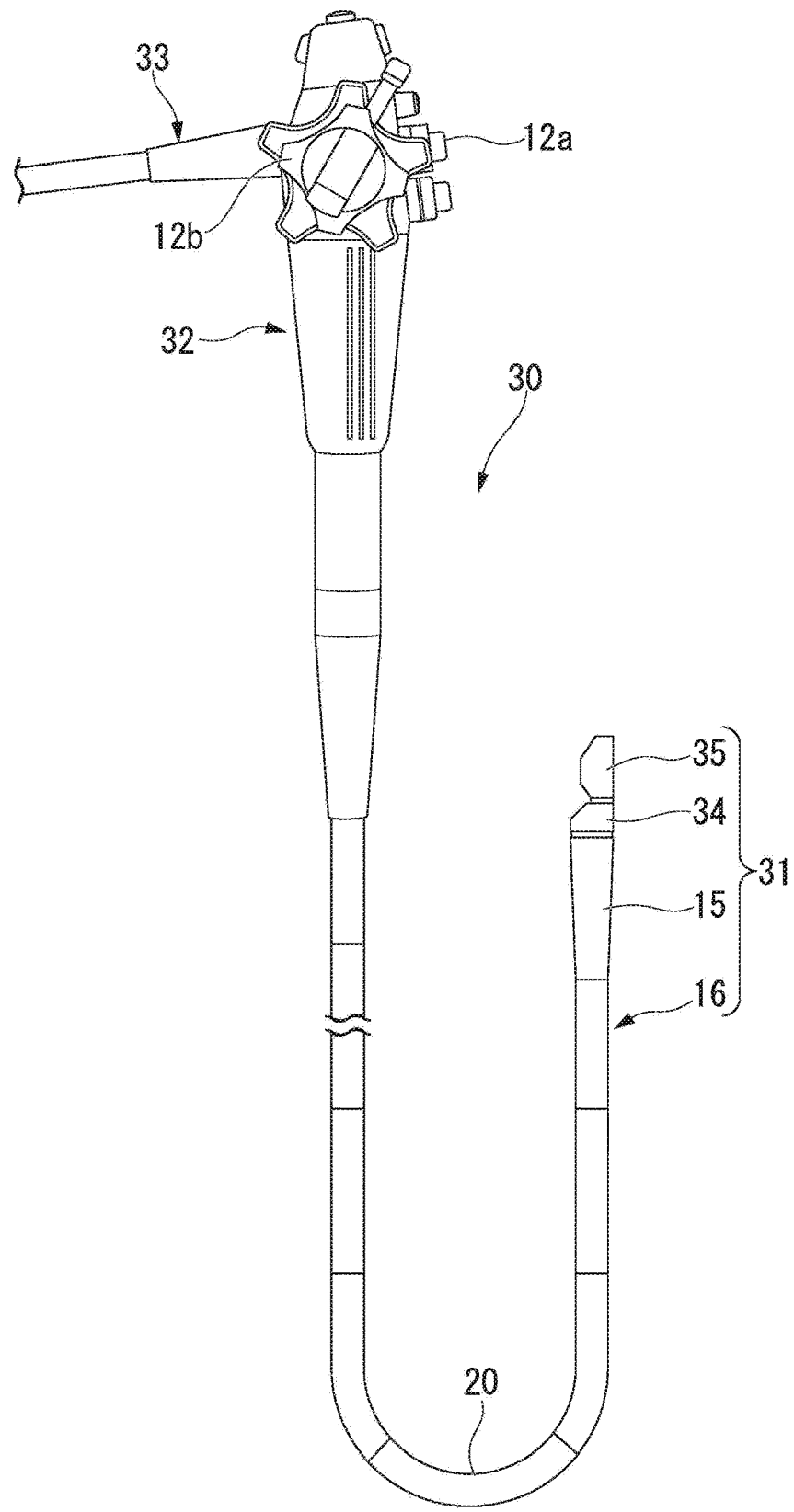
FIG. 5 is a schematic front view showing an example of the configuration of an ultrasound endoscope that is a medical device of a second embodiment of the invention.
Figure 6:
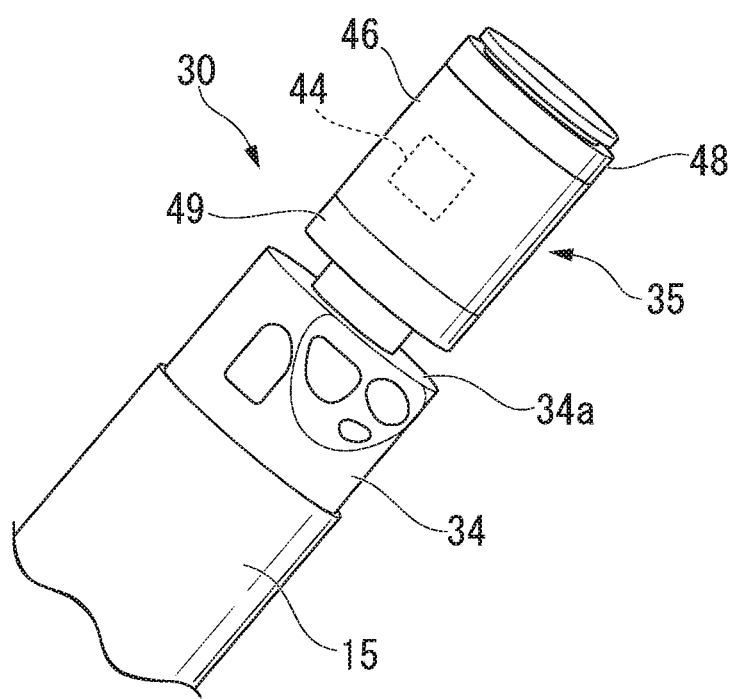
FIG. 6 is a schematic perspective view showing examples of the ultrasound endoscope, which is the medical device of the second embodiment of the invention, and an acoustic lens.
Figure 7:
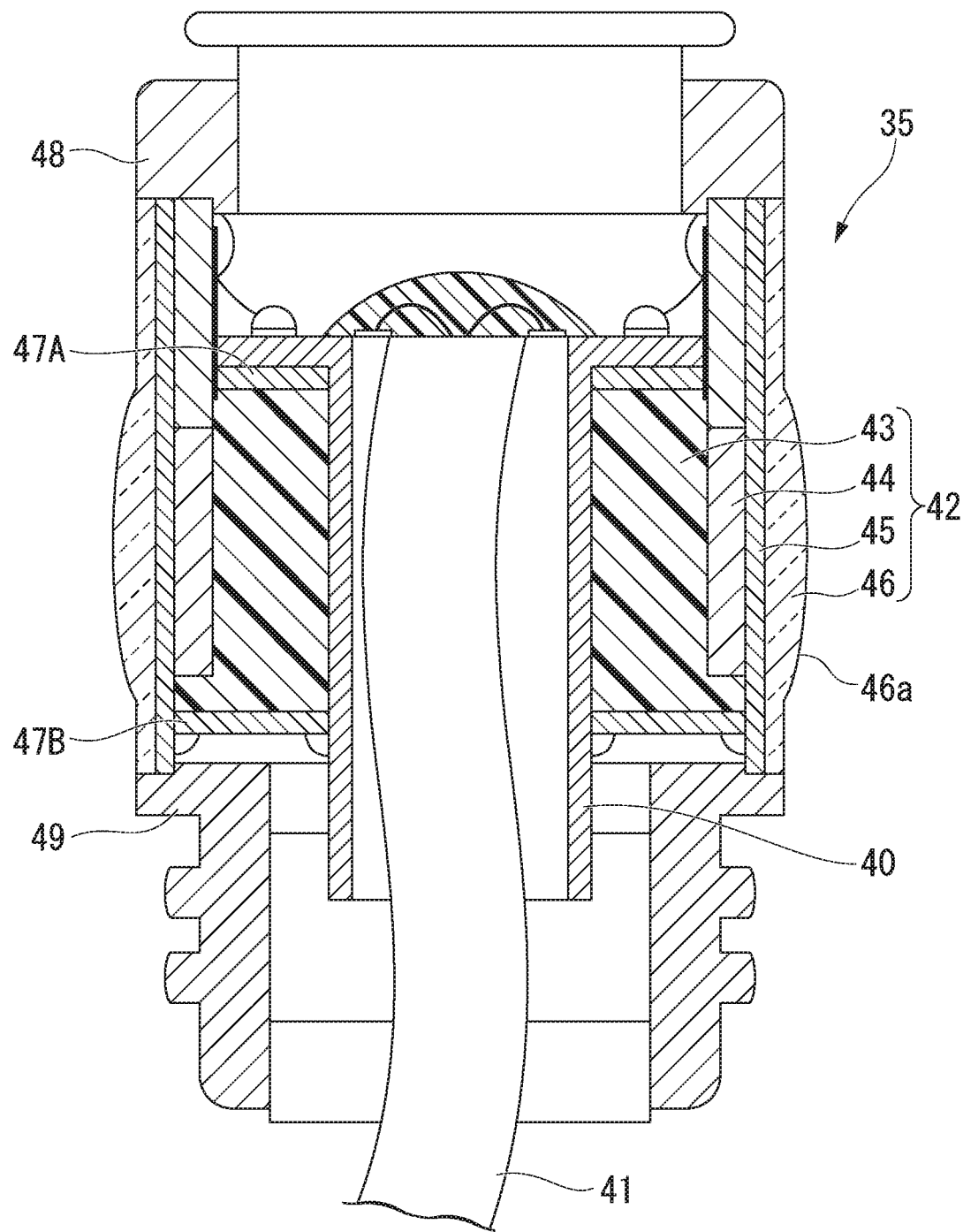
FIG. 7 is a schematic cross-sectional view showing an example of the acoustic lens of the second embodiment of the invention.

FIG. 5 is a schematic front view showing an example of the configuration of an ultrasound endoscope that is a medical device of the second embodiment of the invention. FIG. 6 is a schematic perspective view showing examples of the ultrasound endoscope, which is the medical device of the second embodiment of the invention, and an acoustic lens. FIG. 7 is a schematic cross-sectional view showing an example of the acoustic lens of the second embodiment of the invention.

As shown in FIG. 5, an ultrasound endoscope 30 (medical device) of this embodiment is a medical endoscope that is used while being inserted into the body of a patient. The ultrasound endoscope 30 can acquire information about an object to be examined by applying ultrasound to the object to be examined.

The ultrasound endoscope 30 is subjected to the same gas low-temperature sterilization as the gas low-temperature sterilization that is performed for the endoscope 10 of the first embodiment.

The ultrasound endoscope 30 includes an insertion unit 31, an operation unit 32, and a universal cord 33. The insertion unit 31 is formed to be long and thin, and is inserted into the body of a patient. The operation unit 32 is connected to the proximal end of the insertion unit 31. The universal cord 33 extends from the operation unit 32.

The insertion unit 31 includes a distal end part 34 instead of the distal end part 14 of the insertion unit 11 of the first embodiment. In addition, an ultrasound probe 35 is added to the distal end of the distal end part 34.

A difference between the first and second embodiments will be mainly described below.

An image pickup element acquiring the video of an object to be examined and an image pickup optical system including an appropriate lens are provided in the distal end part 34 shown in FIG. 6 as in the distal end part 14 of the first embodiment. The distal end part 34 has a columnar appearance like the distal end part 14 of the first embodiment. An image pickup window, an illumination window, an opening, and the like are provided on the side surface of the distal end part 34. The opening communicates with the treatment tool channel.

The ultrasound probe 35 is part of the device that emits ultrasound to an object to be examined. The ultrasound probe 35 is used while being in contact with the object to be examined.

The ultrasound probe 35 protrudes forward from a distal end face 34a of the distal end part 34. The appearance of the ultrasound probe 35 has a substantially cylindrical shape.

As shown in FIG. 7, a cylindrical member 40 is disposed in the ultrasound probe 35. The cylindrical member 40 is a member that holds ultrasound transducers 42 to be described later. A coaxial cable 41 is inserted into the cylindrical member 40. The coaxial cable 41 is electrically connected to the ultrasound transducers 42 to be described later. The coaxial cable 41 is inserted into the distal end part 14, the bendable part 15, and the flexible tube 20 like the respective long members of the first embodiment. The coaxial cable 41 extends up to the operation unit 32.

A plurality of ultrasound transducers 42 are arranged in the circumferential direction of the cylindrical member 40 on the outer peripheral portion of the cylindrical member 40. The number of the ultrasound transducers 42 is not particularly limited. In this embodiment, for example, the ultrasound transducers 42 are arranged at two positions facing each other with the central axis of the cylindrical member 40 interposed therebetween.

Each of the ultrasound transducers 42 includes a piezoelectric element 43, a backing member 44, an acoustic matching layer 45, an acoustic lens 46, and electrodes (not shown).

The piezoelectric element 43 generates ultrasound vibration in a case where a voltage is applied by the electrodes (not shown). The shape of the piezoelectric element 43 of this embodiment is the shape of a flat plate.

The backing member 44 is a member for absorbing vibration, which is applied to the inside in a radial direction, of the ultrasound vibration that is generated from the piezoelectric element 43. The backing member 44 is filled between the cylindrical member 40 and the piezoelectric element 43. The backing member 44 is interposed between annular members 47A and 47B in an axial direction. The cylindrical member 40 is inserted into the annular members 47A and 47B.

A resin material having appropriate vibration absorbing properties is used as the material of the backing member 44.

The acoustic matching layer 45 is a layered portion that reduces a difference between the acoustic impedance of an object to be examined and the acoustic impedance of the piezoelectric element 43. In a case where the acoustic impedance of the acoustic matching layer 45 is appropriately set according to the acoustic impedance of the object to be examined, the reflection of ultrasound on the object to be examined is reduced.

The acoustic matching layer 45 covers at least the piezoelectric element 43 as seen in the radial direction. The acoustic matching layer 45 may be formed of a single layer. The acoustic matching layer 45 may be formed of a plurality of layers.

The acoustic lens 46 is molded in an appropriate shape in order to focus ultrasound. The acoustic lens 46 focuses ultrasound, which is transmitted to the outside in the radial direction through the acoustic matching layer 45, of ultrasound generated from the piezoelectric element 43. The acoustic lens 46 emits the focused ultrasound to the outside.

In this embodiment, the shape of the acoustic lens 46 is a substantially cylindrical shape as a whole. The acoustic lens 46 covers the acoustic matching layer 45 from the outside in the radial direction. A lens surface 46a of the acoustic lens 46 is a curved surface that is convex outward in a range where the acoustic lens 46 overlaps at least the piezoelectric element 43 as seen in the radial direction. The acoustic lens 46 extends in the shape of a belt continues in the circumferential direction even in a range where the acoustic lens 46 does not overlap the piezoelectric element 43 in the radial direction.

The acoustic matching layer 45 and the acoustic lens 46 are fixed to casings 48 and 49 made of a resin.

The acoustic lens 46 forms part of the outermost surface of the ultrasound probe 35 together with the casings 48 and 49.

As shown in FIG. 5, the operation unit 32 is part of the device that is used by an operator in order to operate the endoscope 10. Examples of an operation using the operation unit 32 include an operation of the ultrasound probe 35 in addition to the same operation as the operation of the operation unit 12 of the first embodiment. An operation switch 12a of the operation unit 32 includes a switch that is operated to apply ultrasound by the ultrasound transducers 42 and to stop applying ultrasound.

The universal cord 33 has the same structure as the universal cord 13 of the first embodiment except that the universal cord 33 further include a power line and a signal line connected to the ultrasound probe 35.

The same resin composition M as that of the first embodiment is used for some or all of the structural members, which are made of a resin, of the ultrasound endoscope 30 having been described above in order to improve sterilization resistance to gas low-temperature sterilization.

For example, the resin composition M may be used for the same structural members of the insertion unit 31 of this embodiment as the structural members of the insertion unit 11 of the first embodiment for which the resin composition M can be used.

For example, the resin composition M may be used for the same structural members of the operation unit 32 and the universal cord 33 of this embodiment as the structural members of the operation unit 12 and the universal cord 13 of the first embodiment for which the resin composition M can be used.

The resin composition M may be used for the respective structural members, which are made of a resin, of the ultrasound probe 35 in the ultrasound endoscope 30.

For example, it is particularly preferable that the acoustic lens 46 positioned on the outermost surface of the ultrasound probe 35 is made of the resin composition M.

However, in a case where silicone elastomer is used for the acoustic lens 46, it is more preferable that a material excellent in chemical resistance, moldability, adhesiveness, and the like is used as the silicone elastomer. In terms of, for example, moldability, it is more preferable that unmillable silicone is used as silicone used for the manufacture of silicone elastomer. In this case, unmillable liquid silicone in which the ion exchanger I is mixed is used as a molding material for the acoustic lens 46. After being poured into a mold that transfers the shape of the acoustic lens 46, the molding material is cured.

Accordingly, in a case where unmillable silicone is used in a step of manufacturing the acoustic lens 46, the acoustic lens 46 is molded in the shape of the acoustic lens 46 and is joined to the acoustic matching layer 45 and the casings 48 and 49.

However, the acoustic lens 46 may be manufactured using millable silicone. In this case, a compound in which the ion exchanger I is added to the millable silicone is molded in the shape of a lens. The molding of the acoustic lens 46 is manufactured in this way. After that, the molding of the acoustic lens 46 is fixed to the acoustic matching layer 45, the casings 48 and 49, and the like.

The coefficient of friction of silicone elastomer excellent in moldability, adhesiveness, and the like tends to be high. A friction reducing agent may be further included in the resin composition M of the acoustic lens 46 in order to reduce the coefficient of friction of the acoustic lens 46.

For example, a solid lubricant, low-friction fine particles, and the like may be used as the friction reducing agent.

Examples of a material suitable as the friction reducing agent include molybdenum disulfide, tungsten disulfide, graphite, graphite fluoride, boron nitride, mica, talc, calcium fluoride, silicon dioxide, fullerene, carbon nanotubes, lead monoxide, gold, silver, tin, lead, copper, polytetrafluoroethylene (PTFE), a perfluoroalkoxy fluororesin (PFA), a polyamide resin, a polyacetal resin, and the like.

One type of material may be used or two or more types of materials may be used as the friction reducing agent.

The ion exchanger I, which is formed of inorganic particles including metal atoms, is included in the resin composition M forming the acoustic lens 46. As a result, for example, the acoustic characteristics of the acoustic lens 46, such as acoustic impedance and an attenuation ratio for ultrasound, are changed according to the content of the ion exchanger I.

The acoustic characteristics of the acoustic lens 46 may be adjusted according to the content of the ion exchanger I.

However, the acoustic characteristics of the acoustic lens 46 may be adjusted by the filler added to the resin composition M.

For example, an inorganic filler may be used as the filler. Examples of an inorganic filler suitable as the filler include silica, alumina, boehmite, cerium oxide, boron nitride, aluminum nitride, magnesium oxide, aluminum hydroxide, zinc oxide, tungsten trioxide, zirconia, diamond, silicon nitride, silicon carbide, sapphire, and the like.

One type of material may be used or two or more types of materials may be used as the filler.

Since the resin composition M is used for structural members made of a resin in the ultrasound endoscope 30 as described above, sterilization resistance to gas low-temperature sterilization is improved as in the first embodiment. Accordingly, the life of the ultrasound endoscope 30 is improved.

Particularly, in a case where the acoustic lens 46 is made of the resin composition M, chemical attack on the matrix resin R of the acoustic lens 46 and the additives, which are contained in the resin composition M, during gas low-temperature sterilization is suppressed by the ion exchanger I. Accordingly, the deterioration of the matrix resin R and the additives caused by gas low-temperature sterilization is suppressed. As a result, the deterioration of the acoustic characteristics of the acoustic lens 46 is prevented despite repeated sterilization treatment.

Since the acoustic lens 46 covers the internal members of the ultrasound probe 35 in this embodiment, structural members positioned on the inner side than the acoustic lens 46 are also protected from gas low-temperature sterilization.

Examples of cases where the resin composition M is used for the endoscope and the ultrasound endoscope have been described in the description of the respective embodiments, but the resin composition M may be used for various medical devices that are to be subjected to gas low-temperature sterilization. For example, the resin composition M may be used for medical devices, such as a treatment tool and an ultrasound diagnostic device.

EXAMPLES

Examples of a resin composition and a medical device corresponding to the respective embodiments will be described below together with Comparative Examples.

Examples 1 to 27

Examples 1 to 27 are example where the matrix resin R of the resin composition M varies.

Table 1 shows the composition of resin compositions of Examples 1 to 27.

TABLE 1

| | Matrix resin | | Ion exchanger | |
|---|---|---|---|---|
| | Type | Parts by mass | Type | Parts by mass |
| Example 1 | Silicone | 100 | Amphoteric ion exchanger A | 0.5 |
| Example 2 | Acrylic | 100 | Amphoteric ion exchanger A | 3 |
| Example 3 | Polyethylene | 100 | Amphoteric ion exchanger A | 3 |
| Example 4 | Polyetheretherketone | 100 | Amphoteric ion exchanger A | 3 |

TABLE 1-continued

| | Matrix resin | | Ion exchanger | |
|---|---|---|---|---|
| | Type | Parts by mass | Type | Parts by mass |
| Example 5 | Polytetrafluoroethylene | 100 | Amphoteric ion exchanger A | 3 |
| Example 6 | Tetrafluoroethylene | 100 | Amphoteric ion exchanger A | 3 |
| Example 7 | Polyvinylidene fluoride | 100 | Amphoteric ion exchanger A | 3 |
| Example 8 | Polychlorotrifluoroethylene | 100 | Amphoteric ion exchanger A | 3 |
| Example 9 | Chlorotrifluoroethylene | 100 | Amphoteric ion exchanger A | 3 |
| Example 10 | Fluorinated elastomer | 100 | Amphoteric ion exchanger A | 0.5 |
| Example 11 | Polycarbonate | 100 | Amphoteric ion exchanger A | 3 |
| Example 12 | Polystyrene | 100 | Amphoteric ion exchanger A | 3 |
| Example 13 | Urethane | 100 | Amphoteric ion exchanger A | 0.5 |
| Example 14 | Polyurethane | 100 | Amphoteric ion exchanger A | 3 |
| Example 15 | Polyphenylsulfone | 100 | Amphoteric ion exchanger A | 3 |
| Example 16 | Polyethersulfone | 100 | Amphoteric ion exchanger A | 3 |
| Example 17 | Polysulfone | 100 | Amphoteric ion exchanger A | 3 |
| Example 18 | Polypropylene | 100 | Amphoteric ion exchanger A | 3 |
| Example 19 | Polyacetal | 100 | Amphoteric ion exchanger A | 3 |
| Example 20 | Polybenzimidazole | 100 | Amphoteric ion exchanger A | 3 |
| Example 21 | Polyvinyl chloride | 100 | Amphoteric ion exchanger A | 0.5 |
| Example 22 | Polyester | 100 | Amphoteric ion exchanger A | 3 |
| Example 23 | Polyamide | 100 | Amphoteric ion exchanger A | 3 |
| Example 24 | Polyamide | 100 | Amphoteric ion exchanger A | 0.1 |
| Example 25 | Polyamide | 100 | Amphoteric ion exchanger A | 30 |
| Example 26 | Polyamide | 100 | Amphoteric ion exchanger A | 0.05 |
| Example 27 | Polyamide | 100 | Amphoteric ion exchanger A | 40 |

Table 2 shows a correspondence relationship between the abbreviated names and trade names of ion exchangers I to be used in the following description.

TABLE 2

| | Component: | Trade name | Maker |
|---|---|---|---|
| Amphoteric ion exchanger A | Zr—Mg—Al-based compound | IXEPLAS (registered trademark)-A1 | Toagosei Co., Ltd. |
| Amphoteric ion exchanger B | Zr—Mg—Al-based compound | IXEPLAS (registered trademark)-A2 | Toagosei Co., Ltd. |
| Amphoteric ion exchanger C | Zr—Bi-based compound | IXE (registered trademark)-6107 | Toagosei Co., Ltd. |

TABLE 2-continued

| | Component: | Trade name | Maker |
|---|---|---|---|
| Anion exchanger B | Mg—Al-based compound | IXE (registered trademark)-770D | Toagosei Co., Ltd. |
| Cation exchanger E | Sb-based compound | IXE (registered trademark)-300 | Toagosei Co., Ltd. |

As shown in Table 2, "Amphoteric ion exchanger A" indicates IXEPLAS (registered trademark)-A1 (trade name; manufactured by Toagosei Co., Ltd.). "Amphoteric ion exchanger B" indicates IXEPLAS (registered trademark)-A2 (trade name; manufactured by Toagosei Co., Ltd.). Both the amphoteric ion exchangers A and B are a Zr—Mg—Al-based inorganic compound.

"Amphoteric ion exchanger C" indicates IXE (registered trademark)-6107 (trade name; manufactured by Toagosei Co., Ltd.). The amphoteric ion exchanger C is a Zr—Bi-based inorganic compound.

"Anion exchanger D" indicates IXE (registered trademark)-770D (trade name; manufactured by Toagosei Co., Ltd.). The anion exchanger D is an Mg—Al-based inorganic compound.

"Cation exchanger E" indicates IXE (registered trademark)-300 (trade name; manufactured by Toagosei Co., Ltd.). The cation exchanger E is a Sb-based inorganic compound.

As shown in Table 1, silicone, acrylic, polyethylene, polyetheretherketone, polytetrafluoroethylene, tetrafluoroethylene, polyvinylidene fluoride, polychlorotrifluoroethylene, chlorotrifluoroethylene, fluorinated elastomer, polycarbonate, polystyrene, urethane, polyurethane, polyphenylsulfone, polyethersulfone, polysulfone, polypropylene, polyacetal, polybenzimidazole, polyvinyl chloride, and polyester are used as matrix resins R of resin compositions M of Examples 1 to 22, respectively.

Polyamide is used as each of matrix resins R of resin compositions M of Examples 23 to 27.

The amphoteric ion exchanger A is used as all of ion exchangers I of the resin compositions M of Examples 1 to 27.

The contents of the ion exchangers I are as shown in Table 1 with respect to 100 parts by mass of the respective matrix resins R. Specifically, all of the contents of the ion exchangers I of Examples 1, 10, 13, and 21 are set to 0.5 parts by mass. All of the contents of the ion exchangers I of Examples 2 to 9, 11, 12, 14 to 20, and 22 are set to 3 parts by mass. The contents of the ion exchangers I of Examples 23 to 27 are set to 3 parts by mass, 0.1 parts by mass, 30 parts by mass, 0.05 parts by mass, and 40 parts by mass, respectively.

Examples 23 to 27 are examples where the content of the ion exchanger I varies under the same condition for the type of the matrix resin R.

Samples for a tensile test and samples for the evaluation of a gas barrier property are manufactured using the respective resin compositions M of Examples 1 to 27.

The samples for a tensile test are molded with the respective resin compositions M in the shape of the eighth tensile test specimen based on JIS K 7161.

The samples for the evaluation of a gas barrier property are molded with the respective resin compositions M in the shape of a rectangular film having a size of 100 mm*100 mm*20 μm.

Comparative Examples 1 to 23

Table 3 shows the composition of resin compositions of Comparative Examples 1 to 23.

TABLE 3

| | Matrix resin | | Ion exchanger | |
|---|---|---|---|---|
| | Type | Parts by mass | Type | Parts by mass |
| Comparative Example 1 | Silicone | 100 | — | — |
| Comparative Example 2 | Acrylic | 100 | — | — |
| Comparative Example 3 | Polyethylene | 100 | — | — |
| Comparative Example 4 | Polyetheretherketone | 100 | — | — |
| Comparative Example 5 | Polytetrafluoroethylene | 100 | — | — |
| Comparative Example 6 | Tetrafluoroethylene | 100 | — | — |
| Comparative Example 7 | Polyvinylidene fluoride | 100 | — | — |
| Comparative Example 8 | Polychlorotrifluoroethylene | 100 | — | — |
| Comparative Example 9 | Chlorotrifluoroethylene | 100 | — | — |
| Comparative Example 10 | Fluorinated elastomer | 100 | — | — |
| Comparative Example 11 | Polycarbonate | 100 | — | — |
| Comparative Example 12 | Polystyrene | 100 | — | — |
| Comparative Example 13 | Urethane | 100 | — | — |
| Comparative Example 14 | Polyurethane | 100 | — | — |
| Comparative Example 15 | Polyphenylsulfone | 100 | — | — |
| Comparative Example 16 | Polyethersulfone | 100 | — | — |
| Comparative Example 17 | Polysulfone | 100 | — | — |
| Comparative Example 18 | Polypropylene | 100 | — | — |
| Comparative Example 19 | Polyacetal | 100 | — | — |
| Comparative Example 20 | Polybenzimidazole | 100 | — | — |
| Comparative Example 21 | Polyvinyl chloride | 100 | — | — |
| Comparative Example 22 | Polyester | 100 | — | — |
| Comparative Example 23 | Polyamide | 100 | — | — |

As shown in Table 3, Comparative Examples 1 to 23 are resin compositions that are formed of only resins corresponding to the matrix resins R of Examples 1 to 23.

The same samples for a tensile test and samples for the evaluation of a gas barrier property as those of Examples are manufactured using the resin compositions of Comparative Examples 1 to 23.

Evaluation of Examples 1 to 27 and Comparative Examples 1 to 23

The evaluation of tensile strength and the evaluation of a hydrogen peroxide-gas barrier property (hereinafter, abbreviated as the evaluation of a gas barrier property) are made for Examples 1 to 27 and Comparative Examples 1 to 23.

The tensile strength [MPa] of the samples for a tensile test not subjected to sterilization treatment and the tensile strength [MPa] of the samples for a tensile test subjected to hydrogen peroxide plasma sterilization are measured in the evaluation of tensile strength. A precision universal testing machine AG-X (trade name; manufactured by Shimadzu Corporation) is used as a tensile tester.

The hydrogen peroxide plasma sterilization is performed 100 times. In the hydrogen peroxide plasma sterilization, each sample for a tensile test is put into STERRAD (registered trademark) NX (registered trademark) (trade name; manufactured by Johnson & Johnson K.K.).

In the evaluation of a gas barrier property, a hydrogen peroxide indicator of which the color is changed due to hydrogen peroxide is sealed using each of the samples for the evaluation of a gas barrier property. The respective samples for the evaluation of a gas barrier property in which the hydrogen peroxide indicators are sealed are subjected to hydrogen peroxide plasma sterilization under the same conditions as the samples for a tensile test. Whenever one-time sterilization treatment ends for each of the samples for the evaluation of a gas barrier property, the change of the color of the hydrogen peroxide indicator is evaluated. The number of times of sterilization treatment having been performed in a case where the color of the hydrogen peroxide indicator is changed is recorded. The respective samples for the evaluation of a gas barrier property in which the hydrogen peroxide indicators are sealed are put into STERRAD (registered trademark) NX (registered trademark) (trade name; manufactured by Johnson & Johnson K.K.), and are exposed to hydrogen peroxide.

[Evaluation Result 1]

Table 4 shows the evaluation results of Examples 1 to 27. Table 5 shows the evaluation results of Comparative Examples 1 to 23.

TABLE 5

| | Evaluation of tensile strength | | | Evaluation of hydrogen peroxide-gas barrier property | Comprehensive evaluation |
|---|---|---|---|---|---|
| | Tensile strength [Mpa] | | Strength retention (S2/S1) [%] | | |
| | Initial stage (S1) | After sterilization (S2) | | | |
| Comparative Example 1 | 5 | 5 | 100.0 | C | C |
| Comparative Example 2 | 50 | 30 | 60.0 | C | C |
| Comparative Example 3 | 30 | 25 | 83.3 | C | C |
| Comparative Example 4 | 80 | 78 | 97.5 | C | C |
| Comparative Example 5 | 30 | 28 | 93.3 | C | C |
| Comparative Example 6 | 35 | 34 | 97.1 | C | C |
| Comparative Example 7 | 50 | 40 | 80.0 | C | C |
| Comparative Example 8 | 35 | 34 | 97.1 | C | C |
| Comparative Example 9 | 40 | 38 | 95.0 | C | C |
| Comparative Example 10 | 5 | 5 | 100.0 | C | C |
| Comparative Example 11 | 65 | 40 | 61.5 | C | C |
| Comparative Example 12 | 45 | 25 | 55.6 | C | C |
| Comparative Example 13 | 5 | 4.5 | 90.0 | C | C |

TABLE 4

| | Evaluation of tensile strength | | | | | |
|---|---|---|---|---|---|---|
| | Tensile strength [Mpa] | | Strength retention (S2/S1) [%] | Strength retention (with respect to Comparative Example) [%] | Evaluation of hydrogen peroxide-gas barrier property | Comprehensive evaluation |
| | Initial stage (S1) | After sterilization (S2) | | | | |
| Example 1 | 4.8 | 4.8 | 100 | 96.0 | A | A |
| Example 2 | 50 | 48 | 96 | 100.0 | A | A |
| Example 3 | 30 | 30 | 100.0 | 100.0 | A | A |
| Example 4 | 80 | 80 | 100.0 | 100.0 | A | A |
| Example 5 | 30 | 30 | 100.0 | 100.0 | A | A |
| Example 6 | 35 | 35 | 100.0 | 100.0 | A | A |
| Example 7 | 50 | 48 | 96.0 | 100.0 | A | A |
| Example 8 | 35 | 35 | 100.0 | 100.0 | A | A |
| Example 9 | 40 | 40 | 100.0 | 100.0 | A | A |
| Example 10 | 4.7 | 4.7 | 100.0 | 94.0 | A | A |
| Example 11 | 65 | 63 | 96.9 | 100.0 | A | A |
| Example 12 | 45 | 43 | 95.6 | 100.0 | A | A |
| Example 13 | 4.6 | 4.5 | 97.8 | 92.0 | A | A |
| Example 14 | 30 | 28 | 93.3 | 100.0 | A | A |
| Example 15 | 60 | 58 | 96.7 | 100.0 | A | A |
| Example 16 | 70 | 68 | 97.1 | 100.0 | A | A |
| Example 17 | 50 | 48 | 96.0 | 100.0 | A | A |
| Example 18 | 35 | 35 | 100.0 | 100.0 | A | A |
| Example 19 | 69 | 67 | 97.1 | 100.0 | A | A |
| Example 20 | 90 | 88 | 97.8 | 100.0 | A | A |
| Example 21 | 45 | 45 | 100.0 | 100.0 | A | A |
| Example 22 | 50 | 47 | 94.0 | 100.0 | A | A |
| Example 23 | 40 | 38 | 95.0 | 100.0 | A | A |
| Example 24 | 40 | 35 | 87.5 | 100.0 | A | B |
| Example 25 | 38 | 38 | 100.0 | 95.0 | A | A |
| Example 26 | 40 | 30 | 75.0 | 100.0 | B | B |
| Example 27 | 30 | 30 | 100.0 | 75.0 | A | B |

TABLE 5-continued

| | Evaluation of tensile strength | | | Evaluation of hydrogen peroxide-gas barrier property | Comprehensive evaluation |
|---|---|---|---|---|---|
| | Tensile strength [Mpa] | | Strength retention (S2/S1) [%] | | |
| | Initial stage (S1) | After sterilization (S2) | | | |
| Comparative Example 14 | 30 | 28 | 93.3 | C | C |
| Comparative Example 15 | 60 | 55 | 91.7 | C | C |
| Comparative Example 16 | 70 | 65 | 92.9 | C | C |
| Comparative Example 17 | 50 | 45 | 90.0 | C | C |
| Comparative Example 18 | 35 | 33 | 94.3 | C | C |
| Comparative Example 19 | 69 | 55 | 79.7 | C | C |
| Comparative Example 20 | 90 | 85 | 94.4 | C | C |
| Comparative Example 21 | 45 | 30 | 66.7 | C | C |
| Comparative Example 22 | 50 | 44 | 88.0 | C | C |
| Comparative Example 23 | 40 | 15 | 37.5 | C | C |

Tensile strength [MPa], strength retention (S2/S1) [%], and strength retention (with respect to Comparative Example) [%] are shown in Table 4 as the results of the evaluation of tensile strength.

Tensile strength [MPa] and strength retention (S2/S1) [%] are shown in Table 5 as the results of the evaluation of tensile strength.

The measured values of the tensile strength of the samples for a tensile test not subjected to sterilization treatment are shown in the column of "initial stage (S1)" of the column of "tensile strength". The measured values of the tensile strength of the samples for a tensile test subjected to hydrogen peroxide plasma sterilization 100 times are shown in the column of "after sterilization (S2)" of the column of "tensile strength".

Ratios of the tensile strength in S2 to the tensile strength in S1 are shown as a percentage in the column of "strength retention (S2/S1)". The strength retention (S2/S1) represents the change of tensile strength after sterilization treatment with respect to tensile strength before sterilization treatment.

Ratios of the tensile strength in S1 of Examples to the tensile strength in S1 of Comparative Examples, to which the matrix resins R correspond, are shown as a percentage in the column of "strength retention (with respect to Comparative Example)". The strength retention (with respect to Comparative Example) represents the degree of the influence of the ion exchanger I on tensile strength before sterilization treatment.

Since a reduction in tensile strength caused by hydrogen peroxide plasma sterilization is 10% or less in a case where the strength retention (S2/S1) is 90% or more, it can be said that sterilization resistance to gas low-temperature sterilization is good.

Ratios of the tensile strength in S1 of Table 4 to the tensile strength in S1 of Table 5 are shown as a percentage in the column of "strength retention (with respect to Comparative Example)" of Table 4. "Strength retention (with respect to Comparative Example)" represents the influence of the addition of the ion exchanger I on the tensile strength.

Since a reduction in tensile strength caused by the addition of the ion exchanger I is 20% or less in a case where the strength retention (with respect to Comparative Example) is 80% or more, it can be said that an influence on mechanical characteristics is small.

The evaluation of a gas barrier property is made as three levels. An evaluation in a case where the color of the hydrogen peroxide indicator is not changed until the sample for the evaluation of a gas barrier property is subjected to sterilization treatment 100 times is defined as "good" ("A" in Table 4). An evaluation in a case where the color of the hydrogen peroxide indicator is changed when the sample for the evaluation of a gas barrier property is subjected to sterilization treatment 10 times or more and less than 100 times is defined as "fair" ("B" in Table 4). An evaluation in a case where the color of the hydrogen peroxide indicator is changed when the sample for the evaluation of a gas barrier property is subjected to sterilization treatment less than 10 times is defined as "no good" ("C" in Table 4).

A comprehensive evaluation is made on the basis of the results of the evaluation of tensile strength and the evaluation of a gas barrier property. A comprehensive evaluation is made in terms of three levels, "good" ("A" in Table 4), "fair" ("B" in Table 4), and "no good" ("C" in Table 4).

With regard to Examples 1 to 27, a comprehensive evaluation is defined as "good" in a case where the strength retention (S2/S1) is 90% or more, the strength retention (with respect to Comparative Example) is 80% or more, and the evaluation of a gas barrier property is "good".

A comprehensive evaluation is defined as "no good" in a case corresponding to any one of a case where the strength retention (S2/S1) is lower than 70%, a case where the strength retention (with respect to Comparative Example) is lower than 70%, and a case where the evaluation of a gas barrier property is "no good".

A comprehensive evaluation is defined as "fair" in a case where a comprehensive evaluation is neither "good" nor "no good".

Comparative Examples 1 to 23 are evaluated under the same determination conditions as the determination conditions for Examples 1 to 27 in a state where the strength retention (with respect to Comparative Example) is regarded as 100%.

Since the strength retention (S2/S1) is 90% or more, the strength retention (with respect to Comparative Example) is 80% or more, and the evaluation of a gas barrier property is "good" in the evaluation of all of Examples 1 to 23 and 25 as shown in Table 4, the comprehensive evaluation of all of Examples 1 to 23 and 25 are "good".

Since the strength retention (S2/S1) is 87.5% and the evaluation of a gas barrier property is "good" in the evaluation of Example 24, the comprehensive evaluation of Example 24 is "fair".

Since the strength retention (S2/S1) is 75% and the evaluation of a gas barrier property is "fair" in the evaluation of Example 26, the comprehensive evaluation of Example 26 is "fair".

Since the strength retention (with respect to Comparative Example) is 75% with regard to the evaluation of Example 27, the comprehensive evaluation of Example 27 is "fair".

Since the evaluation of a gas barrier property is "no good" in the evaluation of all of Comparative Examples 1 to 23 as shown in Table 5, the comprehensive evaluation of all of Comparative Examples 1 to 23 is "no good". Particularly, the evaluation of Comparative Examples 2, 11, 12, 21, and 23 is also "no good" in that the strength retention (S2/S1) is less than 70%.

From these evaluation results, the degree of a reduction in strength, which is caused by sterilization treatment, in all of the resin compositions M of Examples 1 to 27 in which the ion exchanger I is added to various matrix resins R is better than that of Comparative Examples 1 to 23.

The gas barrier properties of all of the resin compositions M of Examples 1 to 27 are better than those of Comparative Examples 1 to 23.

Examples 23 to 27 are examples where the content of the ion exchanger I vary in a case where the matrix resin R is polyamide.

The evaluation result of a gas barrier property is "good" in the evaluation of Example 24. However, the tensile strength of Example 24 after sterilization is 87.5% and does not reach 90%. It is thought that the sample for evaluation of Example 24 is affected by the chemical attack of sterilization gas since the content of the ion exchanger I is 0.1 parts by mass, i.e., low.

The evaluation result of a gas barrier property is "fair" and tensile strength after sterilization is relatively low in the evaluation of Example 26. It is thought that the sample for evaluation of Example 26 is affected by the chemical attack of sterilization gas since the content of the ion exchanger I is 0.05 parts by mass, i.e., low. There is a concern that cracks and the like where sterilization gas permeates may be generated in the sample for evaluation of Example 26.

A reduction in strength caused by the influence of sterilization treatment hardly occurs and a gas barrier property is also good in the evaluation of Example 27. It is thought that the reason for this is that the content of the ion exchanger I is 40 parts by mass, i.e., high. However, it is thought that a reduction in tensile strength in the initial stage with respect to Comparative Example is large since the content of the ion exchanger I is high.

Examples 29 to 33

Examples 29 to 33 are examples of the flexible tube 20 of the first embodiment. However, the indexes 22A and 22B and the coating layer 23 of the flexible tube 20 will be omitted in the samples for evaluation of Examples 29 to 33 to be described later.

Table 6 shows the composition and the evaluation results of resin compositions M of Examples 29 to 33 and the composition and the evaluation results of a resin composition of Comparative Example 25. [0081]

As shown in Table 6, the respective resin compositions M contain a common matrix resin R in Examples 29 to 33. However, the types and content of the ion exchangers I of the respective resin compositions M of Examples 29 to 33 vary.

Thermoplastic polyester elastomer is used as the matrix resin R of each of Examples 29 to 33. Specifically, Hytrel (registered trademark) (trade name; manufactured by Du Pont-Toray Co., Ltd.) is used as the matrix resin R. Hytrel (registered trademark) (trade name; manufactured by Du Pont-Toray Co., Ltd.) is polybutylene terephthalate (PBT)-based thermoplastic polyester elastomer.

25 parts by mass of the cation exchanger E with respect to 100 parts by mass of the matrix resin R is used as the ion exchanger I of Example 29.

The amphoteric ion exchanger C is used as each of the ion exchangers I of Examples 30 to 32, and the contents of the ion exchangers I of Examples 30 to 32 are set to 25 parts by mass, 0.01 parts by mass, and 5 parts by mass with respect to 100 parts by mass of the matrix resin R.

5 parts by mass of the amphoteric ion exchanger A with respect to 100 parts by mass of the matrix resin R is used as the ion exchanger I of Example 33.

The flexible tubes 20 of samples for evaluation are manufactured using the respective resin compositions M. Specifically, a mixture in which the matrix resin R and the ion exchanger I are contained by the above-mentioned contents is used as a molding material. The molding material is kneaded by a continuous kneading extruder and is then extruded and molded on the outer periphery of the core of the flexible tube 20 of which a spiral tube is covered with a net-like tube. As a result, the outer periphery of the core of the flexible tube 20 is covered with the molding material.

The outer diameter, the length, and the thickness of a tube body 21 of the obtained sample for evaluation is 13 mm, 200 mm, and 0.7 mm, respectively.

The samples for evaluation of Examples and Comparative Example have flexibility, hardness, and appearance that allow the samples for evaluation to be used as a flexible tube for an endoscope.

Comparative Example 25

As shown in Table 6, the sample for evaluation of Comparative Example 25 is manufactured in the same manner as that of Example 29 using the same resin composition as Example 29 except that an ion exchanger is not included.

TABLE 6

| | Matrix resin | | Ion exchanger | | Evaluation | | | |
|---|---|---|---|---|---|---|---|---|
| | Type | Parts by mass | Type | Parts by mass | Appearance | Sterilization resistance | Protection of contents | Comprehensive evaluation |
| Example 29 | Thermoplastic polyester elastomer | 100 | Cation exchanger E | 25 | A | A | A | A |
| Example 30 | Thermoplastic polyester elastomer | 100 | Amphoteric ion exchanger C | 25 | A | AA | AA | A |
| Example 31 | Thermoplastic polyester elastomer | 100 | Amphoteric ion exchanger C | 0.01 | AA | A | A | A |
| Example 32 | Thermoplastic polyester elastomer | 100 | Amphoteric ion exchanger C | 5 | A | AA | AA | A |
| Example 33 | Thermoplastic polyester elastomer | 100 | Amphoteric ion exchanger A | 5 | AA | AA | AA | AA |
| Comparative Example 25 | Thermoplastic polyester elastomer | 100 | — | — | AA | C | C | C |

Evaluation of Examples 29 to 33 and Comparative Example 25

The evaluation of appearance, the evaluation of sterilization resistance, and the evaluation of the protection of contents are made for Examples 29 to 33 and Comparative Example 25.

The samples for evaluation not yet subjected to sterilization treatment are visually checked by an evaluator to make the evaluation of appearance.

The evaluation of sterilization resistance and the evaluation of the protection of contents are made after the samples for evaluation are subjected to hydrogen peroxide plasma sterilization treatment.

The hydrogen peroxide plasma sterilization is performed 200 times for each sample for evaluation. In the hydrogen peroxide plasma sterilization, each sample for evaluation is put into STERRAD (registered trademark) NX (registered trademark).

The appearance of each sample for evaluation subjected to sterilization treatment is visually evaluated in the evaluation of sterilization resistance.

A hydrogen peroxide indicator is inserted into each sample for evaluation in the evaluation of the protection of contents. An end portion of the sample for evaluation is sealed so that hydrogen peroxide does not enter the end portion. Each sample for evaluation in which the hydrogen peroxide indicator is sealed is subjected to the above-mentioned hydrogen peroxide plasma sterilization. Then, the change of the color of the hydrogen peroxide indicator is evaluated.

[Evaluation Result 2]

As shown in Table 6, each evaluation is made in terms of three levels, "very good" ("AA" in Table 6), "good" ("A" in Table 6), and "no good" ("C" in Table 6).

In the evaluation of appearance, an evaluation in a case where the appearance of the sample for evaluation is glossy and is in a uniform state without patterns is defined as "very good". An evaluation in a case where the appearance of the sample for evaluation is uniformly whitened due to the light scattering of the ion exchanger is defined as "good". An evaluation in a case where the appearance of the sample for evaluation has non-uniform patterns and white portions caused by the light scattering of the ion exchanger is defined as "no good".

In the evaluation of sterilization resistance, an evaluation in a case where the appearance of the sample for evaluation subjected to sterilization is glossy is defined as "very good". An evaluation in a case where the appearance of the sample for evaluation loses gloss and is tarnished is defined as "good". An evaluation in a case where any one of defects in which the appearance of the sample for evaluation is chapped, looks white, and becomes rough, a resin is melted and deformed, the resin becomes brittle and broken, and cracks are generated is defined as "no good".

In the evaluation of the protection of contents, an evaluation where the color of the hydrogen peroxide indicator is not changed is defined as "very good". An evaluation where the color of the hydrogen peroxide indicator is changed but is in an allowable range is defined as "good". An evaluation where the color of the hydrogen peroxide indicator is changed to be unallowed is defined as "no good".

A comprehensive evaluation is made on the basis of the results of the evaluation of appearance, the evaluation of sterilization resistance, and the evaluation of the protection of contents. A comprehensive evaluation where all the results of the evaluation are "very good" is defined as "very good". A comprehensive evaluation where "no good" is not present among the results of the evaluation and at least one evaluation is "good" is defined as "good". A comprehensive evaluation in a case where at least one evaluation is "no good" among the results of the evaluation is defined as "no good".

"No good" is not present in all the evaluations of Examples 29 to 33, but the evaluation of sterilization resistance and the evaluation of the protection of contents of Comparative Example 25 are "no good".

The comprehensive evaluations of Examples 29 to 32 are "good". The comprehensive evaluation of Example 33 is "very good". The comprehensive evaluation of Comparative Example 25 is "no good".

Even though the samples for evaluation of Examples 29 to 33 are made of the resin composition M including the ion exchanger I as described above, the samples for evaluation have the appearance required for the flexible tube 20. In addition, the samples for evaluation of Examples 29 to 33 are excellent in sterilization resistance to hydrogen peroxide gas sterilization and are also excellent in the protection of contents positioned in the flexible tube 20.

In contrast, Comparative Example 25 is significantly inferior in sterilization resistance to hydrogen peroxide gas sterilization and the protection of contents.

When Examples 29 and 30 are compared with each other, the amphoteric ion exchanger is more preferable than the cation exchanger in terms of sterilization resistance and the protection of contents where the content of the ion exchanger I is constant.

When Examples 30 to 33 are compared with each other, sterilization resistance and the protection of contents are very preferable where the content of the ion exchanger I is in the range of 5 parts by mass to 25 parts by mass (Examples 30 and 32). However, when the content of the ion exchanger I is 0.01 parts by mass (Example 31), sterilization resistance and the protection of contents are slightly inferior to those of Examples 30 and 32 even though they are in the allowable range.

STERRAD (registered trademark) NX (registered trademark) is used in this evaluation by way of example. STERRAD (registered trademark) NX (registered trademark) is a sterilization device that performs hydrogen peroxide plasma sterilization treatment.

According to the investigation of the inventors of the present invention, although the results of the evaluation are not particularly shown, substantially the same evaluation is obtained even when sterilization treatment is performed by, for example, V-PRO (registered trademark) maX (trade name; manufactured by STERIS Japan Inc.) or STERIZONE (registered trademark) (trade name; manufactured by $TSO_3$ inc.). V-PRO (registered trademark) maX (trade name; manufactured by STERIS Japan Inc.) and STERIZONE (registered trademark) (trade name; manufactured by $TSO_3$ inc.) are sterilization devices using hydrogen peroxide gas.

Examples 34 to 38

Examples 34 to 38 are examples of the resin composition M particularly suitable for the coating layer 23 of the first embodiment.

Table 7 shows the composition and the evaluation results of resin compositions M of Examples 34 to 38 and the composition and the evaluation results of a resin composition of Comparative Example 26.

TABLE 7

| | Matrix resin | | Ion exchanger | | | Evaluation | | |
|---|---|---|---|---|---|---|---|---|
| | Type | Parts by mass | Type | Particle size (μm) | Parts by mass | Gas barrier property | Light transmittance (%) | Comprehensive evaluation |
| Example 34 | Fluorinated coating material | 100 | Cation exchanger E | 0.5 | 0.03 | B | 75 | B |
| Example 35 | Fluorinated coating material | 100 | Amphoteric ion exchanger A | 0.5 | 0.03 | A | 75 | A |
| Example 36 | Fluorinated coating material | 100 | Amphoteric ion exchanger A | 0.5 | 4 | AA | 55 | A |
| Example 37 | Fluorinated coating material | 100 | Amphoteric ion exchanger A | 0.5 | 0.1 | AA | 70 | A |
| Example 38 | Fluorinated coating material | 100 | Amphoteric ion exchanger B | 0.2 | 0.1 | AA | 90 | AA |
| Comparative Example 26 | Fluorinated coating material | 100 | — | — | — | C | 95 | C |

As shown in Table 7, the respective resin composition M contains a common matrix resin R in Examples 34 to 38. However, the types and contents of the ion exchangers I of the respective resin compositions M of Examples 34 to 38 vary.

A fluorinated coating material is used as the matrix resin R of each of Examples 34 to 38. Specifically, LUMIFLON (registered trademark) (trade name; manufactured by AGC Inc.) are used as the matrix resin R.

0.03 parts by mass of the cation exchanger E with respect to 100 parts by mass of the matrix resin R is used as the ion exchanger I of Example 34. The particle size of the cation exchanger E is 0.5 μm as a median diameter.

The amphoteric ion exchanger A is used as each of the ion exchangers I of Examples 35 to 37, and the particle size of the amphoteric ion exchanger A is 0.5 μm as a median diameter. The contents of the ion exchangers I of Examples 35 to 37 are set to 0.03 parts by mass, 4 parts by mass, and 0.1 parts by mass with respect to 100 parts by mass of the matrix resin R.

0.1 parts by mass of the amphoteric ion exchanger B with respect to 100 parts by mass of the matrix resin R is used as the ion exchanger I of Example 38. The particle size of the amphoteric ion exchanger B is 0.2 μm as a median diameter.

The samples for the evaluation of a gas barrier property and the samples for the evaluation of optical transparency of Examples 34 to 38 are manufactured using the respective resin compositions M.

In each sample for the evaluation of a gas barrier property, a base material sheet is coated with each resin composition M. Hytrel (registered trademark) (trade name; manufactured by Du Pont-Toray Co., Ltd.) is used as the material of the base material sheet. Hytrel (registered trademark) (trade name; manufactured by Du Pont-Toray Co., Ltd.) is PBT-based thermoplastic polyester elastomer. A molding, which is formed of a rectangular film having a size of 50 mm*50 mm*0.3 mm, is used as the base material sheet.

In each sample for the evaluation of a gas barrier property, the base material sheet is coated with each resin composition M. The coating thickness of each resin composition M is set to 5 μm.

In each sample for the evaluation of optical transparency, the surface of a slide glass is coated with each resin composition M. The coating thickness of each resin composition M is set to 5 μm.

Comparative Example 26

As shown in Table 7, the sample for the evaluation of a gas barrier property and the sample for the evaluation of optical transparency of Comparative Example 26 are manufactured in the same manner as that of Example 34 using the same resin composition as Example 34 except that an ion exchanger is not included.

Evaluation of Examples 34 to 38 and Comparative Example 26

The evaluation of a gas barrier property and the evaluation of optical transparency are made for Examples 34 to 38 and Comparative Example 26.

In the evaluation of a gas barrier property, a hydrogen peroxide indicator of which the color is changed due to hydrogen peroxide is sealed using each of the samples for the evaluation of a gas barrier property. The respective samples for the evaluation of a gas barrier property in which the hydrogen peroxide indicators are sealed are subjected to hydrogen peroxide gas plasma sterilization. In the hydrogen peroxide gas plasma sterilization, the respective samples for the evaluation of a gas barrier property are put into STERRAD (registered trademark) NX (registered trademark) (trade name; manufactured by Johnson & Johnson K.K.).

Whenever each sterilization treatment ends, the change of the color of the hydrogen peroxide indicator is evaluated.

The number of times of sterilization treatment for each sample for the evaluation of a gas barrier property is recorded where the color of the hydrogen peroxide indicator is changed.

In the evaluation of optical transparency, the light transmittance of each sample for the evaluation of optical transparency is measured after the manufacture of each sample for the evaluation of optical transparency.

[Evaluation Result 3] As shown in Table 7, in the evaluation of a gas barrier property, an evaluation where the color of the hydrogen peroxide indicator is not changed until the sample for the evaluation of a gas barrier property is subjected to sterilization treatment 100 times is defined as "very good" ("AA" in Table 7). An evaluation in a case where the color of the hydrogen peroxide indicator is changed when the sample for the evaluation of a gas barrier property is subjected to sterilization treatment 50 times or more and less than 100 times is defined as "good" ("A" in Table 7).

An evaluation where the color of the hydrogen peroxide indicator is changed when the sample for the evaluation of a gas barrier property is subjected to a sterilization treatment 10 times or more and less than 50 is defined as "fair" ("B"

in Table 7), and an evaluation where the color of the hydrogen peroxide indicator is changed when the sample for the evaluation of a gas barrier property is subjected to sterilization treatment less than 10 times is defined as "no good" ("C" in Table 7).

The results of the evaluation of optical transparency are shown by the measured values of light transmittance (%). Optical transparency required for the coating layer 23 has only to allow the indexes 22A and 22B to be visually recognized. For this reason, as long as light transmittance is 50% or more, this light transmittance is suitable as the light transmittance of the coating layer 23.

A comprehensive evaluation is made on the basis of the results of the evaluation of a gas barrier property and the evaluation of optical transparency. A comprehensive evaluation is performed to evaluate the above-mentioned results by four levels similar to the evaluation of a gas barrier property.

A comprehensive evaluation in a case where the evaluation of a gas barrier property is "very good" and light transmittance is 90% or more is defined as "very good". A comprehensive evaluation where the evaluation of a gas barrier property is "good" and light transmittance is 50% or more or a case where the evaluation of a gas barrier property is "very good" and light transmittance is equal to or higher than 50% and lower than 90% is defined as "good".

A comprehensive evaluation in a case where the evaluation of a gas barrier property is "fair" and light transmittance is 50% or more is defined as "fair". A comprehensive evaluation where the evaluation of a gas barrier property is "no good" or light transmittance is lower than 50% is defined as "no good".

Since the evaluation of a gas barrier property is "fair" and light transmittance is 75% in Example 34, the comprehensive evaluation of Example 34 is "fair". Since the evaluation of a gas barrier property is "good" or "very good" and light transmittance is in the range of 55% to 75% in Examples 35 to 37, the comprehensive evaluations of Examples 35 to 37 are "good". Since the evaluation of a gas barrier property is "very good" and light transmittance is 90% in Example 38, the comprehensive evaluation of Example 38 is "very good".

In contrast, since light transmittance is 95% and was good but a gas barrier property is "no good" in Comparative Example 26, the comprehensive evaluation of Comparative Example 26 is "no good".

When Examples 34 and 35 are compared with each other, it is found that the amphoteric ion exchanger A is better than the cation exchanger E in terms of a gas barrier property.

When Examples 35 to 37 are compared with each other, the gas barrier property is more preferable as the content of the ion exchanger I is higher. However, light transmittance is lower as the content of the ion exchanger I is higher.

When Examples 37 and 38 are compared with each other, light transmittance is higher as a particle size is smaller in a case where the content of the ion exchanger I is constant.

Example 39

Example 39 is an example of the sheath tube 15a of the first embodiment.

Table 8 shows the composition and the evaluation results of a resin composition M of Example 39 and the composition and the evaluation results of a resin composition of Comparative Example 27.

TABLE 8

|  | Matrix resin | | Ion exchanger | | Additive | | | Comprehensive evaluation |
|---|---|---|---|---|---|---|---|---|
|  | Type | Parts by mass | Type | Parts by mass | Cross-linker (parts by mass) | Filler (parts by mass) | Coloring agent (parts by mass) | Sterilization resistance |
| Example 39 | Fluorinated elastomer | 100 | Amphoteric ion exchanger A | 5 | 2 | 10 | 0.7 | A |
| Comparative Example 27 | Fluorinated elastomer | 100 | — | — | 2 | 10 | 0.7 | C |

As shown in Table 8, fluorinated elastomer is used as the matrix resin R and the amphoteric ion exchanger A is used as the ion exchanger I in a resin composition M of Example 39. 5 parts by mass of the ion exchanger I of the resin composition M with respect to 100 parts by mass of the matrix resin R is contained.

In addition, a cross-linker, a filler, and a coloring agent are contained in the resin composition M of Example 39 as additives. Specifically, a peroxide-based cross-linker is used as the cross-linker.

The contents of the cross-linker, the filler, and the coloring agent are set to 2 parts by mass, 10 parts by mass, and 0.7 parts respectively by mass with respect to 100 parts by mass of the matrix resin R.

The resin composition M of Example 39 is molded to manufacture a cylindrical sheath tube 15a having an outer diameter of 5 mm, a length of 50 mm, and a thickness of 0.3 mm as a sample for evaluation.

Comparative Example 27

As shown in Table 8, a sample for evaluation of Comparative Example 27 is manufactured in the same manner as that of Example 39 using the same resin composition as Example 39 except that an ion exchanger is not included.

Evaluation of Example 39 and Comparative Example 27

The evaluation of sterilization resistance is made for Example 39 and Comparative Example 27.

The evaluation of sterilization resistance is made in the same manner as the above-mentioned evaluation of a gas barrier property made for Examples 1 to 27 and the like except that a sample for evaluation varies.

[Evaluation Result 4]

Table 8 shows the results of the evaluation of sterilization resistance. The evaluation criteria are the same as those of the above-mentioned evaluation of a gas barrier property made for Examples 1 to 27 and the like. Specifically, an evaluation where the color of the hydrogen peroxide indicator is not changed until the sample for evaluation is subjected to sterilization treatment 100 times is defined as "good" ("A" in Table 8). An evaluation in a case where the color of the hydrogen peroxide indicator is changed when the sample for evaluation is subjected to sterilization treatment 10 times or more and less than 100 times is defined as "fair" (not applicable in Table 8). An evaluation in a case where the color of the hydrogen peroxide indicator is changed when the sample for evaluation is subjected to sterilization treatment less than 10 times is defined as "no good" ("C" in Table 8).

The sterilization resistance of Example 39 is "good". In contrast, the sterilization resistance of Comparative Example 27 is "no good".

Since the ion exchanger I is contained in the resin composition M of Example 39 as described above, Example 39 is more preferable than Comparative Example 27 in terms of sterilization resistance.

Examples 40 to 47

Examples 40 to 47 are examples of the acoustic lens 46 of the second embodiment.

Table 9 shows the composition and the evaluation results of resin compositions M of Examples 40 to 47 and the composition and the evaluation results of resin compositions of Comparative Examples 28 and 29.

The resin composition M of Example 42 is the same as that of Example 40 except that the matrix resin R is changed into 100 parts by mass of silicone.

The resin composition M of Examples 43 and 44 is the same as that of Example 42 except that the amphoteric ion exchanger C and the amphoteric ion exchanger A are used as the ion exchangers I, respectively. The particle sizes (median diameters) of the amphoteric ion exchanger C and the amphoteric ion exchanger A are 1.5 μm and 0.5 μm, respectively.

The resin composition M of Example 45 is the same as that of Example 43 except that the content of the amphoteric ion exchanger C is 0.5 parts by mass.

Resin compositions M of Examples 46 and 47 are the same as that of Example 45 except that the contents of the amphoteric ion exchangers C is 10 parts by mass and 40 parts by mass, respectively.

Samples for the evaluation of acoustic characteristics, samples for the evaluation of penetration strength, and samples for the evaluation of a gas barrier property of Examples 40 to 47 are manufactured using the respective resin compositions M.

The samples for the evaluation of acoustic characteristics are specimens based on an immersion multiple reflection method, which does not use a comparative measurement

TABLE 9

| | Matrix resin | | Ion exchanger | | | Evaluation | | | | |
|---|---|---|---|---|---|---|---|---|---|---|
| | Type | Parts by mass | Type | Particle size (μm) | Parts by mass | Attenuation ratio | Acoustic impedance | Penetration strength | Gas barrier property | Comprehensive evaluation |
| Example 40 | Polystyrene | 100 | Anion exchanger D | 6 | 0.3 | A | A | A | A | A |
| Example 41 | Polystyrene | 100 | Anion exchanger D | 6 | 50 | A | A | A | A | A |
| Example 42 | Silicone | 100 | Anion exchanger D | 6 | 0.3 | A | A | AA | A | A |
| Example 43 | Silicone | 100 | Amphoteric ion exchanger C | 1.5 | 0.3 | AA | A | AA | A | A |
| Example 44 | Silicone | 100 | Amphoteric ion exchanger A | 0.5 | 0.3 | AA | A | AA | A | A |
| Example 45 | Silicone | 100 | Amphoteric ion exchanger C | 1.5 | 0.5 | AA | AA | AA | AA | AA |
| Example 46 | Silicone | 100 | Amphoteric ion exchanger C | 1.5 | 10 | AA | AA | AA | AA | AA |
| Example 47 | Silicone | 100 | Amphoteric ion exchanger C | 1.5 | 40 | AA | AA | AA | AA | AA |
| Comparative Example 28 | Polystyrene | 100 | — | — | — | AA | A | C | C | C |
| Comparative Example 29 | Silicone | 100 | — | — | — | AA | A | AA | C | C |

As shown in Table 9, polystyrene is used as the matrix resin R in a resin composition M of Example 40 and the anion exchanger D is used as the ion exchanger I in the resin composition M of Example 40.

Specifically, 0.3 parts by mass of the anion exchanger D is added to 100 parts by mass of REXOLITE (registered trademark) 1422 (trade name; manufactured by Ensinger Inc.) in the resin composition M of Example 40. REXOLITE (registered trademark) 1422 (trade name; manufactured by Ensinger Inc.) is polystyrene. The particle size (median diameter) of the anion exchanger D is 6 μm.

The resin composition M of Example 41 is the same as that of Example 40 except that the content of the anion exchanger D is 50 parts by mass.

specimen, of a method of measuring the ultrasonic attenuation coefficient of solid: JIS Z 2354. Specifically, the respective resin compositions M are molded in the shape of a sheet having a size of 30 mm*30 mm*1 mm as the samples for the evaluation of acoustic characteristics.

The respective resin compositions M are molded in the shape of a sheet having a size of 30 mm*30 mm*0.5 mm as the samples for the evaluation of penetration strength.

The samples for the evaluation of a gas barrier property are manufactured in the same manner as the samples for the evaluation of a gas barrier property of the above-mentioned Examples 1 to 27 using the resin compositions M of Examples 40 to 47.

Comparative Examples 28 and 29

As shown in Table 9, Comparative Examples 28 and 29 are formed of the same resin compositions as those of Examples 40 and 42 except that ion exchangers are not included.

The samples for the evaluation of acoustic characteristics, the samples for the evaluation of penetration strength, and the samples for the evaluation of a gas barrier property of Comparative Examples 28 and 29 are manufactured in the same manners as Examples 40 and 42 using the resin compositions of Comparative Examples 28 and 29.

Evaluation of Examples 40 to 47 and Comparative Examples 28 and 29

The evaluation of an attenuation ratio, the evaluation of acoustic impedance, the evaluation of penetration strength, and the evaluation of a gas barrier property are made for Examples 40 to 47 and Comparative Examples 28 and 29.

Methods based on an immersion multiple reflection method, which does not use a comparative measurement specimen, of a method of measuring the ultrasonic attenuation coefficient of solid: JIS Z 2354 are used as methods of measuring an attenuation ratio and acoustic impedance (=medium density*sound speed). In this case, the ultrasound transducers for measurement are driven at a frequency of 5 MHz.

As shown in Table 9, in the evaluation of an attenuation ratio, an evaluation in case where an attenuation ratio is 7 dB/cm/MHz or less is defined as "very good" ("AA" in Table 9). An evaluation in a case where an attenuation ratio exceeds 7 dB/cm/MHz and is equal to or lower than 10 dB/cm/MHz is defined as "good" ("A" in Table 9). An evaluation where an attenuation ratio exceeded 10 dB/cm/MHz is defined as "no good" ("C" in Table 9).

In the evaluation of acoustic impedance, an evaluation where acoustic impedance is in the range of $1.4*10^6$ N·s/m$^3$ to $1.6*10^6$ N·s/m$^3$ is defined as "very good" ("AA" in Table 9). An evaluation in a case where acoustic impedance is equal to or higher than $1.2*10^6$ N·s/m$^3$ and lower than $1.4*10^6$ N·s/m$^3$ or exceeded $1.6*10^6$ N·s/m$^3$ and is equal to or lower than $1.8*10^6$ N·s/m$^3$ is defined as "good" ("A" in Table 9). An evaluation where acoustic impedance is lower than $1.2*10^6$ N·s/m$^3$ or exceeded $1.8*10^6$ N·s/m$^3$ is defined as "no good" ("C" in Table 9).

In the evaluation of penetration strength, first, the samples for the evaluation of penetration strength are subjected to hydrogen peroxide plasma sterilization treatment.

The hydrogen peroxide plasma sterilization is performed 50 times. In the hydrogen peroxide plasma sterilization, each sample for the evaluation of penetration strength is put into STERRAD (registered trademark) NX (registered trademark).

Penetration strength is measured on the basis of JIS Z 1707:1997. Specifically, when a test needle having a diameter of 1 mm penetrated the sample for the evaluation of penetration strength having subjected to sterilization treatment, the maximum load applied to the test needle is measured. The measured value of the maximum load is divided by the thickness of the sample for the evaluation of penetration strength, so that penetration strength is calculated.

In the evaluation of penetration strength, an evaluation where penetration strength is 25 N/mm or more is defined as "very good" ("AA" in Table 9). An evaluation where penetration strength is equal to or higher than 20 N/mm and lower than 25 N/mm is defined as "good" ("A" in Table 9). An evaluation where penetration strength is lower than 20 N/mm is defined as "no good" ("C" in Table 9).

In the evaluation of a gas barrier property, first, the samples for the evaluation of a gas barrier property is subjected to hydrogen peroxide plasma sterilization treatment.

The hydrogen peroxide plasma sterilization is performed 100 times. In the hydrogen peroxide plasma sterilization, each sample for the evaluation of a gas barrier property is put into STERRAD (registered trademark) NX (registered trademark).

Whenever one-time sterilization treatment ends for each of the samples for the evaluation of a gas barrier property, the change of the color of the hydrogen peroxide indicator is evaluated. The number of times of sterilization treatment having been performed where the color of the hydrogen peroxide indicator is changed is recorded.

In the evaluation of a gas barrier property, an evaluation where the color of the hydrogen peroxide indicator is not changed until the sample for the evaluation of a gas barrier property is subjected to sterilization treatment 100 times is defined as "very good" ("AA" in Table 9). An evaluation where the color of the hydrogen peroxide indicator is changed when the sample for the evaluation of a gas barrier property is subjected to sterilization treatment 70 times or more and less than 100 times is defined as "good" ("A" in Table 9). An evaluation where the color of the hydrogen peroxide indicator is changed when the sample for the evaluation of a gas barrier property is subjected to sterilization treatment less than 70 times is defined as "no good" ("C" in Table 9).

A comprehensive evaluation is made on the basis of the results of the evaluation of an attenuation ratio, the evaluation of acoustic impedance, the evaluation of penetration strength, and the evaluation of a gas barrier property. A comprehensive evaluation in a case where all the results of the above-mentioned evaluation are "very good" is defined as "very good". A comprehensive evaluation in a case where "no good" is not present among the results of the above-mentioned evaluation and at least one evaluation is "good" is defined as "good". A comprehensive evaluation in a case where at least one evaluation is "no good" among the results of the above-mentioned evaluation is defined as "no good".

[Evaluation Result 5]

As shown in Table 9, "no good" is not present among all the evaluation results of Examples 40 to 47. The comprehensive evaluations of Examples 40 to 44 are "good". The comprehensive evaluations of Examples 45 to 47 are "very good".

In contrast, since the evaluation of penetration strength and the evaluation of a gas barrier property in Comparative Example 28 are "no good", the comprehensive evaluation of Comparative Example 28 is "no good". Since the evaluation of a gas barrier property in Comparative Example 29 is "no good", the comprehensive evaluation of Comparative Example 29 is "no good".

An attenuation ratio is significantly affected by the particle size of the ion exchanger I. Attenuation ratios in cases where the particle size is 1.5 µm or less (Examples 43 to 47) are more preferable than attenuation ratios where the particle size is 6 µm (Examples 40 to 42). It is thought that the reason for this is that ultrasound is attenuated due to an increase in the scattering of ultrasound as a particle size is larger. In a case where the matrix resin R is polystyrene, every evaluation is "good". However, an evaluation where the matrix resin R is silicone is "very good" in a case where the content of the ion exchanger I is in the range of 0.5 parts by mass to 40 parts by mass.

The evaluation of penetration strength is "very good" when the matrix resin R is silicone and the ion exchanger I is added. However, the evaluation of penetration strength is "no good" when a resin composition included only polystyrene (Comparative Example 28), and penetration strength is improved when the ion exchanger I is added (Examples 40 and 41).

In a case where the matrix resin R is silicone, the evaluation of penetration strength is "very good" as described above in not only Examples but also Comparative Example 29. However, an evaluation where the ion exchanger I is not included even though the matrix resin R is silicone (Comparative Example 29) is "no good" in the evaluation of a gas barrier property. An evaluation where the content of the ion exchanger I is 0.3 parts by mass (Examples 42 to 44) is "good" in the evaluation of a gas barrier property. Accordingly, it is thought that deterioration is caused by sterilization gas in a case where the ion exchanger I is not included even though the matrix resin R is silicone.

In Examples 44 to 47, the evaluation of a gas barrier property is also "very good". Accordingly, it is thought that sterilization resistance is improved in a case where the content of the ion exchanger I is in the range of 0.5 parts by mass to 40 parts by mass. According to Examples 44 to 47, since Examples 44 to 47 are preferable in gas barrier property, the deterioration of contents, which are positioned in the ultrasound probe 35, caused by sterilization gas is prevented.

The respective preferred embodiments and the respective examples of the invention have been described above, but the invention is not limited to the respective embodiments and the respective examples. Elements can be added, omitted, and substituted, and the other modifications may be applied without departing from the scope of the invention.

Further, the invention is not limited by the above description and is limited by only accompanying claims.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A medical device to be subjected to gas low-temperature sterilization comprising:
   a resin composition comprising urethane or polyurethane and an ion exchanger.

2. The medical device according to claim 1, wherein, in the resin composition, the ion exchanger contains an inorganic substance that discharges at least one of a hydroxide ion and a proton.

3. The medical device according to claim 1, wherein, in the resin composition, a content of the ion exchanger is in a range of 0.01 parts by mass to 40 parts by mass with respect to 100 parts by mass of the resin urethane or polyurethane.

4. A flexible tube for a medical device to be subjected to gas low-temperature sterilization, the flexible tube comprising:
   a resin composition comprising urethane or polyurethane and an ion exchanger.

5. A medical device to be subjected to gas low-temperature sterilization comprising:
   the flexible tube according to claim 4.

6. The medical device according to claim 5, wherein the medical device is an endoscope comprising an operation part configured to be operated by a user and an insertion part configured to be inserted into a patient, and
   wherein the insertion part comprises a distal end part, a bendable part, and the flexible tube, in order from a distal end side of the insertion part.

7. The medical device according to claim 6, the medical device is an endoscope comprising an operation part configured to be operated by a user and an insertion part configured to be inserted into a patient, and
   wherein the ultrasound probe is provided at a distal end of the insertion part.

8. A flexible tube for a medical device to be subjected to gas low-temperature sterilization, the flexible tube comprising:
   a resin composition comprising a fluorinated elastomer and an ion exchanger.

9. A medical device to be subjected to gas low-temperature sterilization comprising:
   the flexible tube according to claim 8.

10. The medical device according to claim 9, wherein the medical device is an endoscope comprising an operation part configured to be operated by a user and an insertion part configured to be inserted into a patient, and
    wherein the insertion part comprises a distal end part, a bendable part, and the flexible tube, in order from a distal end side of the insertion part.

11. An acoustic lens for a medical device to be subjected to gas low-temperature sterilization, the acoustic lens comprising:
    a resin composition comprising silicone and an ion exchanger.

12. A medical device to be subjected to gas low-temperature sterilization comprising:
    the acoustic lens according to claim 11.

13. The medical device according to claim 12, wherein the medical device includes an ultrasound probe comprising an ultrasound transducer, wherein the ultrasound transducer includes a piezoelectric element, a backing member, an acoustic matching layer, and the acoustic lens.

14. A sheath for a medical device to be subjected to gas low-temperature sterilization, the sheath comprising:
    a resin composition comprising a fluorinated elastomer and an ion exchanger.

15. A medical device to be subjected to gas low-temperature sterilization comprising:
    the sheath according to claim 14.

16. The medical device according to claim 15, wherein the medical device is an endoscope comprising an operation part configured to be operated by a user and an insertion part configured to be inserted into a patient,
    wherein the insertion part comprises a distal end part, a bendable part, and a flexible tube, in order from a distal end side of the insertion part, and
    wherein the bendable part comprises the sheath.

17. A sheath for a medical device to be subjected to gas low-temperature sterilization, the sheath comprising:
    a resin composition comprising urethane or polyurethane and an ion exchanger.

18. A medical device to be subjected to gas low-temperature sterilization comprising:
    the sheath according to claim 17.

19. The medical device according to claim 18, wherein the medical device is an endoscope comprising an operation part configured to be operated by a user and an insertion part configured to be inserted into a patient,
wherein the insertion part comprises a distal end part, a bendable part, and a flexible tube, in order from a distal end side of the insertion part, and
wherein the bendable part comprises the sheath.

* * * * *